US011183278B2

(12) United States Patent
White et al.

(10) Patent No.: US 11,183,278 B2
(45) Date of Patent: *Nov. 23, 2021

(54) LIQUID MEASUREMENT SYSTEMS, APPARATUS, AND METHODS OPTIMIZED WITH TEMPERATURE SENSING

(71) Applicant: Bigfoot Biomedical, Inc., Milpitas, CA (US)

(72) Inventors: James White, Cambridge, MA (US); Richard Whalley, Cambridge, MA (US); Kevin Sihlanick, Cambridge, MA (US); Matthew Legrand, Cambridge, MA (US)

(73) Assignee: BIGFOOT BIOMEDICAL, INC., Milpitas, CA (US)

( * ) Notice: Subject to any disclaimer, the term of this patent is extended or adjusted under 35 U.S.C. 154(b) by 28 days.

This patent is subject to a terminal disclaimer.

(21) Appl. No.: 16/280,656

(22) Filed: Feb. 20, 2019

(65) Prior Publication Data

US 2020/0027533 A1 Jan. 23, 2020

Related U.S. Application Data

(63) Continuation of application No. 14/816,634, filed on Aug. 3, 2015, now Pat. No. 10,255,991.

(Continued)

(51) Int. Cl.
*G01F 22/00* (2006.01)
*G16H 10/60* (2018.01)
(Continued)

(52) U.S. Cl.
CPC ........... *G16H 10/60* (2018.01); *A61B 5/1495* (2013.01); *A61B 5/14532* (2013.01);
(Continued)

(58) Field of Classification Search
None
See application file for complete search history.

(56) References Cited

U.S. PATENT DOCUMENTS 4,286,646 A 9/1981 Tauber et al.
4,857,738 A 8/1989 Myers et al.
(Continued)

FOREIGN PATENT DOCUMENTS

CN 1906485 A 1/2007
CN 101262950 A 9/2008
(Continued)

OTHER PUBLICATIONS

Office Action dated Jul. 2, 2020 for Chinese Application No. 201910115230.5, with English translation, 18 pages.
(Continued)

*Primary Examiner* — Alexander A Mercado
(74) *Attorney, Agent, or Firm* — Hamre, Schumann, Mueller & Larson, P.C.

(57) ABSTRACT

An apparatus for measuring liquid volume in a container includes a plurality of light sources for emitting electromagnetic radiation (EMR) toward the container, a plurality of sensors optically coupleable to the plurality of light sources, each sensor of the plurality of sensors for detecting the EMR emitted by at least a portion of the plurality of light sources, a temperature sensor for measuring at least one temperature associated with a liquid in the container, and at least one processor for receiving data representative of the portion of the detected EMR from each of the plurality of sensors, comparing the at least one measured temperature to a temperature guideline to identify any temperature events associated with the received data; normalizing the received data based on any temperature events associated with the received data; and converting the normalized data into a
(Continued)

signature representative of the EMR detected by the plurality of sensors.

18 Claims, 26 Drawing Sheets

Related U.S. Application Data

(60) Provisional application No. 62/032,017, filed on Aug. 1, 2014.

(51) Int. Cl.

| | | |
|---|---|---|
| *G01K 13/02* | (2021.01) | |
| *G01F 23/00* | (2006.01) | |
| *G01F 23/292* | (2006.01) | |
| *G01F 23/296* | (2006.01) | |
| *A61M 5/32* | (2006.01) | |
| *A61B 5/157* | (2006.01) | |
| *A61B 5/145* | (2006.01) | |
| *A61B 5/1495* | (2006.01) | |
| *G16H 20/17* | (2018.01) | |

(52) U.S. Cl.
CPC ........... *A61B 5/157* (2013.01); *A61M 5/3202* (2013.01); *G01F 22/00* (2013.01); *G01F 23/0015* (2013.01); *G01F 23/2921* (2013.01); *G01F 23/2961* (2013.01); *G01K 13/02* (2013.01); *A61B 2560/0252* (2013.01); *A61M 2205/3306* (2013.01); *A61M 2205/3368* (2013.01); *A61M 2205/3379* (2013.01); *A61M 2205/3553* (2013.01); *A61M 2205/3561* (2013.01); *A61M 2205/3592* (2013.01); *A61M 2205/52* (2013.01); *A61M 2205/581* (2013.01); *A61M 2205/582* (2013.01); *A61M 2205/583* (2013.01); *A61M 2205/8212* (2013.01); *A61M 2230/201* (2013.01); *G01K 13/026* (2021.01); *G16H 20/17* (2018.01)

(56) References Cited

U.S. PATENT DOCUMENTS

| | | | | |
|---|---|---|---|---|
| 4,904,878 A * | 2/1990 | Gipp | ................ | G01F 23/2921 |
| | | | | 250/577 |
| 4,952,055 A | 8/1990 | Wyatt | | |
| 4,956,560 A * | 9/1990 | Smith, Jr. | ................ | B67C 3/20 |
| | | | | 250/223 B |
| 5,065,037 A | 11/1991 | Finney et al. | | |
| 5,184,510 A * | 2/1993 | Rossman | ............ | G01F 23/0076 |
| | | | | 73/1.73 |
| 5,303,585 A | 4/1994 | Lichte | | |
| 5,452,076 A * | 9/1995 | Schopper | ............... | G01F 23/292 |
| | | | | 356/128 |
| 5,556,002 A | 9/1996 | Green | | |
| 5,569,212 A | 10/1996 | Brown | | |
| 5,593,390 A | 1/1997 | Castellano et al. | | |
| 5,606,125 A * | 2/1997 | Lyons | ................ | G01F 23/2921 |
| | | | | 73/293 |
| 5,628,309 A | 5/1997 | Brown | | |
| 5,720,733 A | 2/1998 | Brown | | |
| 5,748,091 A | 5/1998 | Kim | | |
| 5,782,814 A | 7/1998 | Brown et al. | | |
| 5,792,117 A | 8/1998 | Brown | | |
| 5,938,642 A | 8/1999 | Burroughs et al. | | |
| 6,068,615 A * | 5/2000 | Brown | ................ | A61M 5/1782 |
| | | | | 604/207 |
| 6,090,473 A | 7/2000 | Yoshikawa et al. | | |
| 6,110,148 A | 8/2000 | Brown et al. | | |
| 6,113,578 A * | 9/2000 | Brown | ............... | G01F 11/027 |
| | | | | 604/207 |
| 6,270,455 B1 | 8/2001 | Brown | | |
| 6,352,523 B1 | 3/2002 | Brown et al. | | |
| 6,452,158 B1 | 9/2002 | Whatley et al. | | |
| 6,505,509 B2 * | 1/2003 | Gualtieri | ............... | G01F 23/284 |
| | | | | 181/124 |
| 6,685,678 B2 | 2/2004 | Evans et al. | | |
| 7,049,622 B1 | 5/2006 | Weiss | | |
| 7,074,209 B2 | 7/2006 | Evans et al. | | |
| 7,115,113 B2 | 10/2006 | Evans et al. | | |
| 7,408,632 B2 | 8/2008 | Moore et al. | | |
| 7,498,563 B2 | 3/2009 | Mandro et al. | | |
| 7,710,567 B1 * | 5/2010 | Mentzer | ............. | G01N 21/8507 |
| | | | | 356/436 |
| 7,772,008 B2 * | 8/2010 | Curtis | ...................... | G01N 1/38 |
| | | | | 436/164 |
| 8,079,245 B1 * | 12/2011 | Owens | ................ | G01F 23/0084 |
| | | | | 73/1.73 |
| 8,197,449 B2 | 6/2012 | Nielsen et al. | | |
| 8,221,356 B2 | 7/2012 | Enggaard et al. | | |
| 8,348,904 B2 | 1/2013 | Petersen | | |
| 8,618,485 B1 | 12/2013 | Lockhart | | |
| 8,817,258 B2 | 8/2014 | Whalley et al. | | |
| 9,138,091 B2 | 9/2015 | Zhao et al. | | |
| 9,250,111 B2 | 2/2016 | Whalley et al. | | |
| 9,255,830 B2 | 2/2016 | Whalley et al. | | |
| 9,638,564 B2 | 5/2017 | Whalley et al. | | |
| 9,642,968 B2 | 5/2017 | Whalley et al. | | |
| 10,183,120 B2 | 1/2019 | Sihlanick et al. | | |
| 10,190,901 B2 | 1/2019 | Whalley et al. | | |
| 10,255,991 B2 | 4/2019 | White et al. | | |
| 10,258,743 B2 | 4/2019 | Whalley et al. | | |
| 10,684,156 B2 | 6/2020 | Whalley et al. | | |
| 10,695,501 B2 | 6/2020 | Whalley et al. | | |
| 2001/0056258 A1 | 12/2001 | Evans | | |
| 2004/0079152 A1 * | 4/2004 | Sorenson | ................ | G01F 23/38 |
| | | | | 73/313 |
| 2004/0089067 A1 * | 5/2004 | Frank | ................ | G01F 23/2921 |
| | | | | 73/293 |
| 2005/0177137 A1 | 8/2005 | Kipfer | | |
| 2006/0154327 A1 * | 7/2006 | Bachur, Jr. | ............. | C12M 41/40 |
| | | | | 435/34 |
| 2006/0178578 A1 * | 8/2006 | Tribble | ................... | B65B 3/003 |
| | | | | 600/432 |
| 2007/0143062 A1 | 6/2007 | Memmott et al. | | |
| 2007/0213949 A1 * | 9/2007 | Artiuch | ...................... | G01F 3/20 |
| | | | | 702/85 |
| 2008/0108885 A1 | 5/2008 | Colvin, Jr. | | |
| 2008/0113337 A1 | 5/2008 | Sakudo et al. | | |
| 2008/0316612 A1 | 12/2008 | Hyde et al. | | |
| 2009/0159654 A1 | 6/2009 | Grimard | | |
| 2009/0299279 A1 * | 12/2009 | Richter | ................. | G01F 11/029 |
| | | | | 604/93.01 |
| 2010/0030136 A1 | 2/2010 | Dacquay et al. | | |
| 2010/0080086 A1 | 4/2010 | Wright et al. | | |
| 2010/0134303 A1 | 6/2010 | Perkins | | |
| 2010/0213392 A1 | 8/2010 | Hatzav et al. | | |
| 2011/0102796 A1 | 5/2011 | Shang et al. | | |
| 2011/0184343 A1 | 7/2011 | Veit et al. | | |
| 2011/0270214 A1 | 11/2011 | Joergensen et al. | | |
| 2011/0292399 A1 | 12/2011 | Alphonse | | |
| 2011/0313395 A1 | 12/2011 | Krulevitch et al. | | |
| 2012/0234074 A1 * | 9/2012 | Hagen | ...................... | G01F 1/32 |
| | | | | 73/1.73 |
| 2012/0268741 A1 * | 10/2012 | Pommereau | ....... | A61M 5/14566 |
| | | | | 356/343 |
| 2013/0030405 A1 | 1/2013 | Hartman et al. | | |
| 2013/0310756 A1 | 11/2013 | Whalley et al. | | |
| 2014/0130745 A1 * | 5/2014 | Van Halsema | .... | G06K 9/00362 |
| | | | | 119/14.08 |
| 2014/0262918 A1 * | 9/2014 | Chu | ........................... | A61J 1/03 |
| | | | | 206/534 |
| 2015/0115158 A1 * | 4/2015 | Fu | ........................... | G01F 23/00 |
| | | | | 250/338.1 |
| 2015/0362350 A1 * | 12/2015 | Miller | ................. | G01F 23/0046 |
| | | | | 73/290 V |
| 2016/0030673 A1 | 2/2016 | White et al. | | |
| 2016/0061646 A1 * | 3/2016 | Mestivier | ................. | G01F 23/14 |
| | | | | 73/1.73 |

(56) References Cited

U.S. PATENT DOCUMENTS

| | | | |
|---|---|---|---|
| 2017/0232204 A1* | 8/2017 | Knapp | A61M 5/28 604/66 |
| 2017/0246399 A1 | 8/2017 | Forlani et al. | |
| 2018/0050157 A1* | 2/2018 | Whalley | G01F 13/00 |
| 2018/0064881 A1 | 3/2018 | Whalley et al. | |
| 2018/0299317 A1 | 10/2018 | Truong et al. | |
| 2019/0137315 A1 | 5/2019 | Whalley et al. | |
| 2019/0336695 A1 | 11/2019 | Sihlanick et al. | |
| 2020/0023134 A1 | 1/2020 | Whalley et al. | |

FOREIGN PATENT DOCUMENTS

| | | |
|---|---|---|
| CN | 102301207 A | 12/2011 |
| CN | 103354800 A | 10/2013 |
| CN | 105716680 A | 6/2016 |
| DE | 10 2006 047537 A1 | 12/2011 |
| EP | 1382946 A1 | 1/2004 |
| EP | 1 920 793 A1 | 5/2008 |
| JP | 2000-279515 A | 10/2000 |
| JP | 2010-505475 A | 2/2010 |
| JP | 2013-126532 A | 6/2013 |
| WO | WO 2010/088591 A2 | 8/2010 |
| WO | WO 2010/098929 A1 | 9/2010 |
| WO | WO 2011/108225 A1 | 9/2010 |
| WO | WO 2011/032960 A1 | 3/2011 |
| WO | WO 2011/084713 A1 | 7/2011 |
| WO | WO 2012/062843 A1 | 5/2012 |
| WO | WO 2012/126975 A1 | 9/2012 |

OTHER PUBLICATIONS

Office Action dated Jul. 3, 2020 for Chinese Application No. 201780043779.7, with English translation, 30 pages.
Appeal Decision dated Mar. 23, 2020 for Japanese Application No. 2015-514106, w/English translation, 24 pages.
Decision of Rejection dated Mar. 16, 2020 for Japanese Application No. 2016-572816, w/English translation, 9 pages.
Non-Final Office Action dated Feb. 4, 2020 for U.S. Appl. No. 16/283,084, 11 pages.
Office Action dated Dec. 11, 2019 for Canadian Application No. 2,874,331, 4 pages.
Communication pursuant to Article 94(3) dated Mar. 22, 2019 from European Application No. 15826907.6, 5 pages.
Notice of Reasons for Rejection dated Apr. 9, 2019 from Japanese Application No. 2016-572816, w/English translation.
Notice of Reasons for Rejection dated Mar. 28, 2019 from Japanese Application No. 2015-514106, w/English translation, 14 pages.
Office Action dated Jan. 17, 2019 from Canadian Application No. 2,874,331, 4 pages.
Communication pursuant to Article 94(3) dated Jan. 31, 2018 issued by the European Patent Office from European Application No. 13793067.3, 6 pages.
Decision of Rejection dated Nov. 1, 2017 from Japanese Application No. 2015-514106, w/English translation, 13 pages.
Office Action dated Jul. 19, 2019 from Chinese Application No. 201580040532.0, w/English translation, 21 pages.
Extended European Search Report dated Jun. 7, 2016 from European Application No. 13793067.3, 21 pages.
Extended European Search Report dated Mar. 8, 2018 from European Application No. 15826907.6, 10 pages.
International Search Report and Written Opinion dated Oct. 21, 2013 from International Application No. PCT/US2013/041982, 10 pages.
International Search Report and Written Opinion dated Nov. 17, 2017 from International Application No. PCT/US2017/041982, 15 pages.
International Search Report and Written Opinion dated Nov. 20, 2015 for International Application No. PCT/US2015/043417, 8 pages.
Notice of Reasons for Rejection dated Feb. 17, 2017 from Japanese Application No. 2015-514106 w/English translation, 15 pages.
Office Action dated Apr. 12, 2017 from Chinese Application No. 201380036003.4 w/English language translation, 15 pages.
Office Action dated Dec. 14, 2018 from Chinese Application No. 201580040532.0, w/English translation, 10 pages.
Office Action dated Jun. 28, 2016 from Chinese Application No. 201380036003.4 w/English language translation, 19 pages.
Office Action dated Mar. 27, 2018 from Chinese Application No. 20130036003.4 w/English translation, 7 pages.
Non-Final Office Action dated Feb. 28, 2014 from U.S. Appl. No. 13/796,889, 10 pages.
Non-Final Office Actions dated Jun. 10, 2015 from U.S. Appl. No. 14/334,181, 12 pages.
Non-Final Office Action dated Jun. 15, 2016 from U.S. Appl. No. 14/982,650, 11 pages.
Non-Final Office Action dated Jun. 17, 2016 from U.S. Appl. No. 14/982,668, 10 pages.
Non-Final Office Action dated Dec. 22, 2017 from U.S. Appl. No. 15/464,466, 12 pages.
Non-Final Office Action dated Jul. 25, 2018 from U.S. Appl. No. 15/477,444, 13 pages.
Non-Final Office Action dated Jun. 11, 2019 for U.S. Appl. No. 16/235,286, 15 pages.
Non-Final Office Action dated Jun. 29, 2018 from U.S. Appl. No. 14/816,634, 15 pages.
Non-Final Office Action dated Feb. 14, 2018 from U.S. Appl. No. 15/649,224, 15 pages.
Non-Final Office Action dated Aug. 29, 2019 from U.S. Appl. No. 16/209,580, 9 pages.
Office Action issued for the Japanese patent application No. 2020-121999, dated Jun. 30, 2021, 7 pages including English translation.

* cited by examiner

LIQUID MEASUREMENT SYSTEMS, APPARATUS, AND METHODS OPTIMIZED WITH TEMPERATURE SENSING

CROSS-REFERENCE TO RELATED APPLICATIONS

This application claims priority to and the benefit of U.S. Provisional Application No. 62/032,017, entitled, "Liquid Measurement System with Temperature Sensor," filed Aug. 1, 2014, the disclosure of which is hereby incorporated by reference in its entirety.

BACKGROUND

The present disclosure relates generally to systems, apparatus, and methods for measuring a quantity of a liquid and/or a temperature of the liquid disposed in a delivery device, and in particular to an injection pen cap that includes a temperature sensor.

Many chronic disease patients are prescribed medications that need to be self-administered, administered by a caregiver, or administered by an automated or semi-automated delivery system using injection pens or similar drug delivery devices. For example, patients diagnosed with Type I or II diabetes must regularly check their blood glucose levels and administer an appropriate dose of insulin using an injection pen. In order to monitor the efficacy of the medication, dose information must be recorded. The process of manually logging dose information, particularly in an uncontrolled setting, is tedious and error prone. Patients often forget to log the dose information when administering medicine. In addition, many such patients may be minors or elderly who cannot efficiently and/or accurately track the dose information.

Incomplete dosage records hinder the ability of a patient to self-manage disease conditions and prevent caregivers from adjusting care plans based on behavioral insights. Lack of adherence to target dosage schedules for injectable medicines may result in an increased need for critical care, which results in a significant increase in health care costs in countries around the world.

Thus, a need exists for improved technological aids, in particular, new delivery devices, to better assist both patients in improving their ability to self-manage disease treatment using drug delivery devices and caregivers in monitoring patient health. In particular, there is a need for systems, apparatus, and methods that facilitate data acquisition on patient behavior and allow that data to be used to reduce the incidence of hospital visits (e.g., re-admission), as well as to inform and educate patients, care providers, family members, and financial service providers.

SUMMARY

Embodiments described herein relate generally to systems, apparatus, and methods for measuring a quantity of a liquid and/or a temperature of the liquid disposed in a delivery device, and in particular to an injection pen cap that includes a temperature sensor. The inventors have recognized and appreciated that temperature may affect properties of embodiments of the systems, apparatus, and methods described herein. In particular, temperature may affect measurements of a quantity of a liquid made using some embodiments. In some embodiments, temperature may affect properties of one or more additional components, such as a glucose meter test strip.

Temperature may also affect the quality of a drug disposed in a drug delivery device. The efficacy and shelf life of medications-including, but not limited to, insulin—are highly impacted by the temperature to which a particular medication is exposed and/or at which a particular medication is stored. Injection pens that contain such medications are often carried by a patient, for example, in a patient's pocket, backpack, purse, luggage, etc. Thus, medications may be exposed to widely fluctuating ambient temperatures which can impact the expiration status of the medications and/or the bioavailability of, bioefficacy of, and/or comfort provided by the medications as ultimately delivered to the patient. Furthermore, knowledge of the specific impact of temperature exposure may allay safety concerns and anxieties of patients, care providers, and family members.

In some embodiments, a dose measurement system for measuring a liquid volume in a container includes a plurality of light sources which are disposed and configured to emit electromagnetic radiation toward the container. A plurality of sensors is optically coupleable to the plurality of light sources. The sensors are disposed and configured to detect the electromagnetic radiation emitted by at least a portion of the light sources. The apparatus includes a temperature sensor configured to measure a temperature of the liquid disposed in the container. The apparatus also includes a processing unit configured to receive data representing the portion of the detected electromagnetic radiation from each of the plurality of sensors and to convert the received data into a signature representative of the electromagnetic radiation detected by the plurality of sensors. The processing unit is also configured to receive temperature information from the temperature sensor and normalize sensor values, determine an efficacy of the liquid, determine an expiration status of the liquid, determine a level of administration comfort, etc. In some embodiments, the temperature sensor is also configured to measure the temperature of the environment surrounding the liquid.

DETAILED DESCRIPTION

Figure 1:
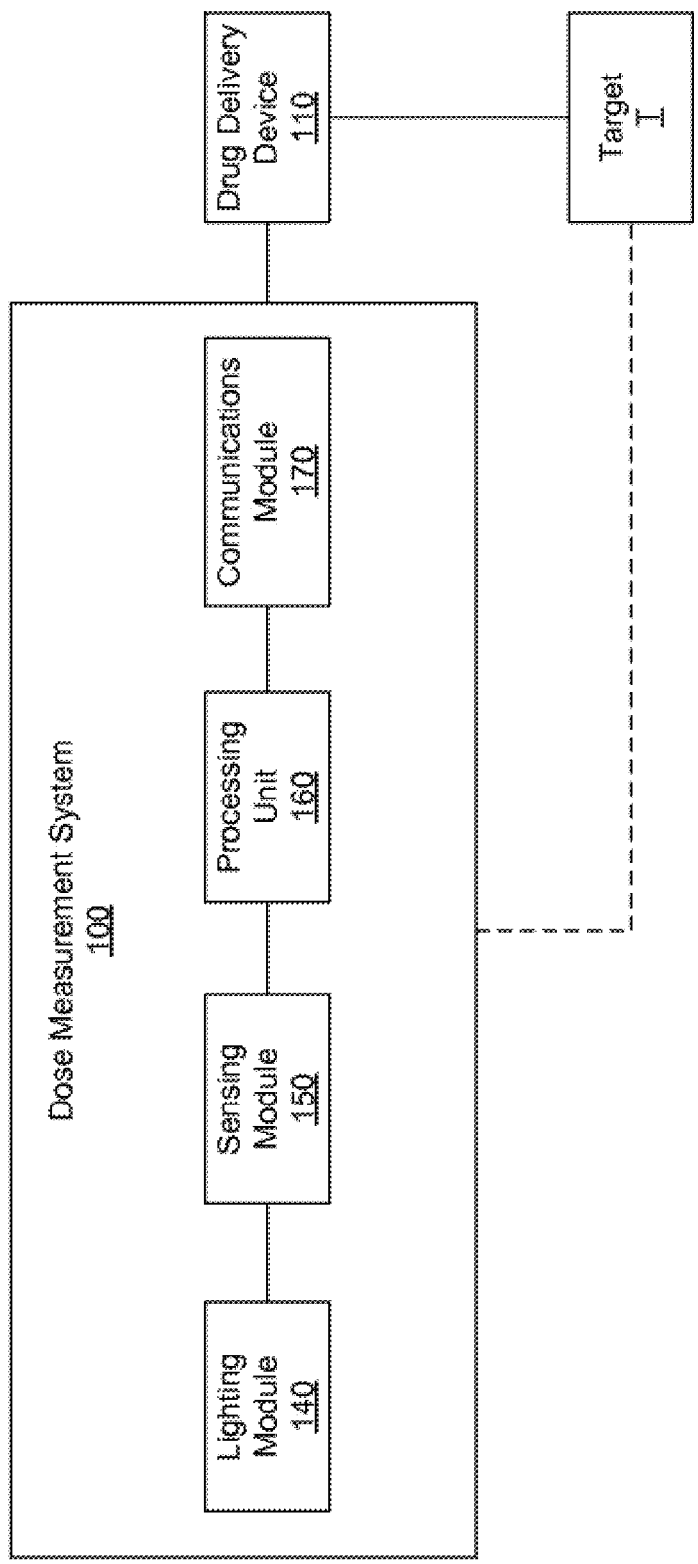
FIG. 1 is a schematic block diagram of a dose measurement system in accordance with some embodiments.

Embodiments described herein relate generally to systems, apparatus, and methods for measuring a quantity of a liquid and/or a temperature of the liquid disposed in a delivery device, and in particular to an injection pen cap that includes a temperature sensor. Many chronic disease patients are prescribed medications that need to be self-administered, administered by a caregiver, or administered by an automated or semi-automated delivery system using injection pens or similar drug delivery devices. For example, patients diagnosed with Type I or II diabetes must regularly check their blood glucose levels and administer an appropriate dose of insulin using an injection pen. In order to monitor the efficacy of the medication, dose information must be recorded. The process of manually logging dose information, particularly in an uncontrolled setting, is tedious and error prone.

Furthermore, temperature may affect measurement properties of some embodiments and quality properties of a drug included in some embodiments. The efficacy and shelf life of medications—including, but not limited to, insulin—are highly impacted by the temperature to which a particular medication is exposed and/or at which a particular medication is stored. Injection pens that contain such medications are often carried by a patient, for example, in a patient's pocket, backpack, purse, luggage, etc. Thus, medications may be exposed to widely fluctuating ambient temperatures which can impact the expiration status of the medications and/or the bioavailability of, bioefficacy of, and/or comfort provided by the medications as ultimately delivered to the patient. Furthermore, knowledge of the specific impact of temperature exposure may allay safety concerns and anxieties of patients, care providers, and family members.

Embodiments of the systems, apparatus, and methods described herein include one or more temperature sensors configured to measure a temperature of the liquid disposed in the container and/or an environment around the liquid including, but not limited to, a container containing the liquid, such as an injection pen.

In some embodiments, a dose measurement system for measuring the liquid volume in a container includes a plurality of light sources which are disposed and configured to emit electromagnetic radiation toward the container. The plurality of light sources may include a plurality of, for example, light-emitting diodes (LEDs). Alternatively, a single light source (e.g., a single LED) may be used to emit electromagnetic radiation into a light pipe that splits the emitted electromagnetic radiation into the plurality of light sources which are disposed and configured to emit electromagnetic radiation toward the container. In some embodiments, a plurality of sensors is optically coupleable to the plurality of light sources and is disposed and configured to detect the electromagnetic radiation emitted by at least a portion of the light sources. The apparatus also includes a processing unit configured to receive data representing the portion of the detected electromagnetic radiation from each of the plurality of sensors and to convert the received data into a signature representative of the electromagnetic radiation detected by the plurality of sensors. One or more temperature sensors are disposed and configured to measure a temperature of the liquid disposed in the container and/or a temperature of the environment surrounding the container. This temperature information may be used to determine a variety of metrics including a level of bioavailability and/or bioefficacy of the remaining liquid.

In some embodiments, a method of estimating a volume of liquid in a drug delivery device includes causing a plurality of light sources to emit electromagnetic radiation toward a drug container and detecting a signature of the emitted electromagnetic radiation through the drug container with a plurality of sensors. The detected signature is then compared to a plurality of reference signatures to determine the volume of liquid in the drug container. Each of the plurality of reference signatures correspond to a volume level remaining in the drug container. In some embodiments, detecting the signature of the emitted electromagnetic radiation through the drug container includes detecting at least a portion of the electromagnetic radiation emitted from at least a portion of the plurality of light sources. The portion of the electromagnetic radiation detected by each of the plurality of sensor devices may be compiled into the signal signature. In some embodiments, the method further includes detecting one or more temperatures of the drug, the container, and/or the environment surrounding the container. One or more detected temperatures may be used to indicate a quality associated with the drug. One or more temperatures also may be used to indicate a quality associated with and/or adjust volume measurement properties.

In some embodiments, the method also includes calculating a dose delivered to a patient based on the volume of liquid in the drug container. In some embodiments, the dose delivered to a patient is compared with a patient medication schedule to monitor compliance. The method may further include correcting the signal signature for background light which can contribute to noise. The correction may include comparing the signal signature with a background signature detected by the plurality of sensors in a dark state of each of the plurality of light sources. The method may further include correcting the signal signature for temperature effects. The correction may include comparing the signal signature with a background signature detected by the plurality of sensors in a preferred temperature state of each of the plurality of light sources. In some embodiments, the method also includes generating the plurality of reference signatures by recording the signature for a range of dose volumes in the drug container. The method may also include associating the signal with the reference signature using probabilistic matching to determine the volume of liquid remaining in the dose container.

In some embodiments, a method for determining a dose delivered by an injection pen using the drug measurement system includes causing a plurality of light sources to emit electromagnetic radiation toward the injection pen a first time and detecting a first signature of the emitted electromagnetic radiation through the injection pen with a plurality of sensors. The first signature is then compared to a plurality of reference signatures to determine the first volume of liquid in the injection pen. The method further includes causing the plurality of light sources to emit electromagnetic radiation toward the injection pen a second time, after the first time, and detecting a second signature of the emitted electromagnetic radiation through the injection pen with the plurality of sensors. The second signature is then compared to the plurality of reference signatures to determine the second volume of liquid in the injection pen. The second volume may be deducted from the first volume to determine a dose delivered from the injection pen.

In some embodiments, the plurality of light sources and the plurality of sensors are disposed in an injection pen cap. In some embodiments, the method includes detecting the first signature prior to the injection pen cap being removed from the injection pen and detecting the second signature after the injection pen cap has been placed back on the injection pen. The method may also include communicating the dose delivered information to an external device. In some embodiments, the method includes switching the pen cap to a power save mode after a predetermined period of inactivity of the pen cap. In some embodiments, the method further includes alerting the user if a volume of liquid remaining in the drug container is critically low and/or if it is time to deliver a dose of medication.

In some embodiments, a health management system includes a drug delivery device including a drug reservoir, and a dose measurement system configured to be removably coupleable to the drug delivery device. The dose measurement system includes a plurality of light sources disposed and configured to emit electromagnetic radiation toward the drug reservoir a plurality of sensors optically coupleable to the plurality of light sources disposed and configured to detect a quantity of electromagnetic radiation communicated through the drug reservoir. The quantity of electromagnetic radiation serves as a signature representative of the volume of liquid remaining in the drug reservoir. The health management system also includes a display configured to present information to a user indicative of the volume of liquid remaining in the drug reservoir. The dose measurement system may be configured to communicate data representative of the volume of liquid remaining in the drug reservoir to a remote device, for example, to allow the remote device to calculate a dose delivered to the patient. In some embodiments, the dose management system is configured to receive user health data from the remote device which may include, for example user blood glucose level, user diet, user exercise, and/or user home health monitored data.

FIG. 1 is a schematic block diagram of a dose measurement system 100 for measuring the dose in a drug delivery device 110 according to some embodiments. The dose measurement system 100 includes a lighting module 140, a sensing module 150, a processing unit 160 and a communications module 170. The dose measurement system 100 may be configured to be removably coupleable to the drug delivery device 110 that is used to deliver a drug dose to a target T such as, for example, a human patient.

The drug delivery device 110 may be any drug delivery device 110 that can be used for injecting a medication into a patient. For example, the drug delivery device 110 may be an injection pen (e.g., insulin injection pen), a syringe, pump (e.g., insulin delivery pump), an ampoule, or a vial. The dose measurement system 100 may be configured to be coupleable to a wide variety of drug delivery devices 110 (e.g., different shapes, sizes, and drug volumes). In some embodiments, the dose measurement system 100 may be configured to receive a portion of the drug delivery device 110 (e.g., a portion that defines an internal volume containing the drug, an injector, and/or plunger). In some embodiments, the dose measurement system 100 is configured to be removable from the drug delivery device 110 when the user is delivering a dose to the target T. In some embodiments, the dose measurement system 110 may remain attached to the drug delivery device 110 when the user is delivering a dose to the target T. In some embodiments, the dose measurement system 100 is configured to be reusable. In some embodiments, the dose measurement system 110 may be permanently coupled to the drug delivery device 110, for example, integrated into the body of the drug delivery device. In such embodiments, the dose measurement system 100 may be disposable.

The lighting module 140 includes a plurality of light sources configured to emit electromagnetic radiation towards the drug delivery device 110. In some embodiments, the plurality of light sources may be configured to emit electromagnetic radiation towards a drug reservoir (not shown) of the drug delivery device 110. In some embodiments, each of the plurality of light sources may be a light emitting diode (LED). In some embodiments, the plurality of light sources may be configured to emit such that the electromagnetic radiation can penetrate through housing and any internal components of the drug delivery device 110, and/or the liquid drug contained therein. In some embodiments, the plurality of light sources may be configured to emit continuous electromagnetic radiation for a predefined time period. In some embodiments, the plurality of light sources may be configured to emit pulses of electromagnetic radiation (e.g., a series of less than 100 microsecond pulses).

The sensing module 150 includes a plurality of sensors that are optically coupleable to the plurality of light sources of the lighting module 140. In some embodiments, the each of the plurality of sensors is a photodetector. The plurality of sensors are disposed and configured to detect the electromagnetic radiation emitted by at least a portion of the light sources. In some embodiments, the detected electromagnetic radiation includes transmitted, refracted and reflected portions of the electromagnetic radiation. In some embodiments, the refracted electromagnetic radiation may include multi-directional refraction caused by a lensing effect of a curved surface of the housing of the drug delivery device 110 and/or the drug reservoir.

The processing unit 160 is configured to receive the electromagnetic radiation signal from the sensing module 150 (i.e., each of the plurality of sensors) and convert the received data into a signal signature representative of the electromagnetic radiation detected by each of the plurality of sensors. The processing unit 160 may include a processor, including, but not limited to, a microcontroller, a microprocessor, an ASIC chip, an ARM chip, an analog to digital convertor (ADC), and/or a programmable logic controller (PLC). In some embodiments, the processing unit 160 may include a memory that is configured to temporarily store at least one of the electromagnetic radiation data detected by each of the plurality of sensors and the signal signature produced from it. In some embodiments, the memory may also be configured to store a plurality of reference signatures. Each of the plurality of reference signatures may be representative of a drug volume in the drug delivery device 110. In some embodiments, the processing unit 160 also includes an RFID chip configured to store information (e.g., the dose remaining information) and allow a near field communication (NFC) device to read the stored information. In some embodiments, the processing unit 160 is configured to associate the signal signature with the reference signature to determine the dose volume remaining in and/or dose injected by the drug delivery device 110. In some embodiments, the processing unit 160 also includes a global positioning, infrared radiation, and/or microwave radiation navigation system (e.g., GPS) to determine a current location of the dose measurement system 100.

The communications module 170 may be configured to allow two-way communication with an external device, including, but not limited to, a smart phone, a local computer, and/or a remote server. In some embodiments, the communications module 170 includes means for wireless communication with an external device, including, but not limited to, Wi-Fi, Bluetooth®, low powered Bluetooth®, ZigBee, and the like. In some embodiments, the communications module 170 includes a communication interface to provide wired communication with an external device (e.g., a USB or firewire interface). In some embodiments, the communication interface also is used to recharge a power source such as a rechargeable battery.

In some embodiments, the communications module 170 includes a display configured to communicate a status of the dose measurement system 100 to the user, including, but not limited to, dose remaining, history of use, remaining battery life, wireless connectivity status, and/or user reminders. In some embodiments, the communications module also includes speakers and/or vibration mechanisms to convey audio and/or tactile alerts. In some embodiments, the communications module 170 includes a user input interface (e.g., a button, a switch, an alphanumeric keypad, a touch screen, a camera, and/or a microphone) to allow a user to input information or instructions into the dose measurement system 100, including, but not limited to, powering ON the system, powering OFF the system, resetting the system, manually inputting details of a patient behavior, manually inputting details of drug delivery device 110 usage, and/or manually initiating communication between the dose measurement system 100 and a remote device.

The dose measurement system 100 may be disposed in a housing (not shown) that is configured to be removably coupleable to the drug delivery device 110. For example, the lighting module 140, sensing module 150, processing unit 160 and the communications module 170 may be incorporated into a housing, or individual components of the dose measurement system 100 (e.g., the lighting module 140 and the sensing module 150) may be incorporated into a first housing and other components (e.g., the processing unit 160 and communications module 170) may be separate or incorporated into a second housing. In some embodiments, the housing is configured (e.g., shaped and sized) to be removably coupled to at least a portion of the drug delivery device 110. For example, the housing may have a recess and/or define a bore into which a portion of the drug delivery device 110 may be received. The housing may have alignment features to allow the dose measurement system 100 to be coupled to the drug delivery device 110 in a predetermined radial orientation. The housing may be opaque and include an insulation structure to prevent interference from ambient electromagnetic radiation to, for example, increase signal quality. For example, the insulation structure may be a metal lining configured to shield the electronic components of the dose measurement system 100 from external electromagnetic radiation. In some embodiments, the housing substantially resembles, for example, a pen cap to act as a replacement cap for the drug delivery device 110 (i.e., an injection pen).

In some embodiments, the lighting module 140 and the sensing module 150 are disposed and/or oriented in the housing of the dose measurement system 100, such that the plurality of light sources are disposed on a first side, and the plurality of sensors are disposed on a second side of the drug delivery device 110. In some embodiments, the plurality of light sources is disposed at a first radial position with respect to the drug delivery device 110 and the plurality of sensors is disposed at a second radial position which is different than the first radial position (e.g., the second radial position may be approximately 180 degrees from the first radial position). In other words, the dose management system 100 may be arranged so that the plurality of light sources is disposed on one side of a drug reservoir and the plurality of sensors is disposed on the opposite side of the drug reservoir. In some embodiments, each of the plurality of light sources and the plurality of sensors is disposed in a substantially straight line. In some embodiments, the plurality of light sources are disposed such that each light source is located adjacent to at least one sensor, each light source also located parallel to and in line of sight of at least one sensor. In some embodiments, at least one of the plurality of light sources and/or at least one of the plurality of sensors is located in an inclined orientation with respect to a longitudinal axis of the drug delivery device 110. In some embodiments, the number of the plurality of sensors is equal to, greater than or less than the number of the plurality of light sources. In some embodiments, the plurality of light sources and the plurality of sensors is configured such that the dose measurement system 110 can detect the volume of drug in the drug delivery device 110 with a resolution of 1 unit of drug or smaller (e.g., fractions of units of drug such as 0.1 units, 0.2 units, 0.5 units, etc.). In some embodiments, the plurality of light sources and the plurality of sensors are configured such that the dose measurement system 110 can detect the position of a plunger portion of an actuator disposed in the drug delivery device 110 with a resolution of 10 micrometers, 20 micrometers, 30 micrometers, 40 micrometers, 50 micrometers, 60 micrometers, 70 micrometers, 80 micrometers, 90 micrometers, 100 micrometers, 110 micrometers, 120 micrometers, 130 micrometers, 140 micrometers, 150 micrometers, 160 micrometers, 170 micrometers, 180 micrometers, or 200 micrometers, inclusive of all ranges there between.

Having described above various general principles, several exemplary embodiments of these concepts are now described. These embodiments are only examples, and many other configurations of a dose measurement system, systems and/or methods for measuring dose delivered by a drug delivery device and overall health of a patient are envisioned.

Figure 2:
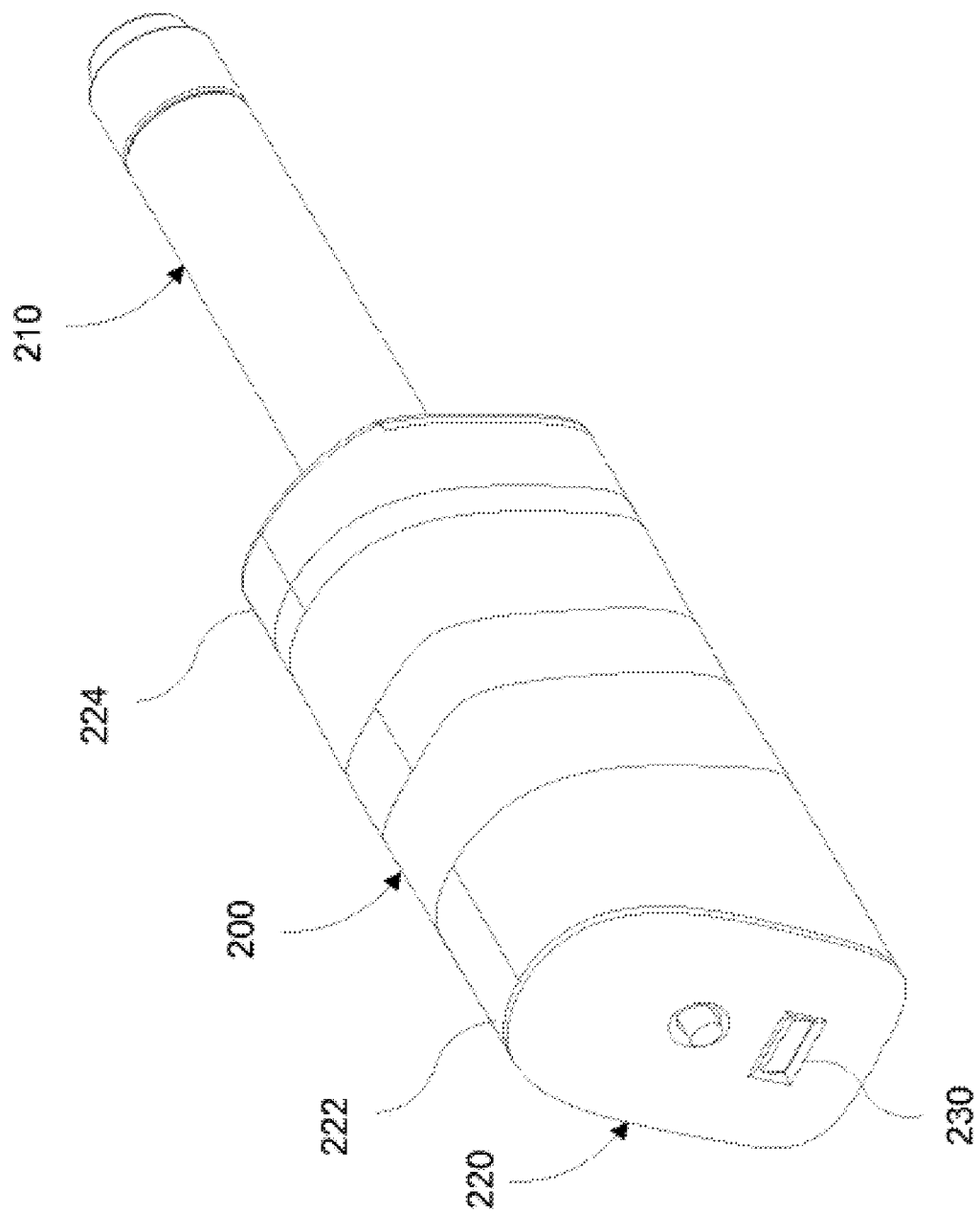
FIG. 2 is a perspective view of a dose measurement system in accordance with some embodiments.
Figure 3:
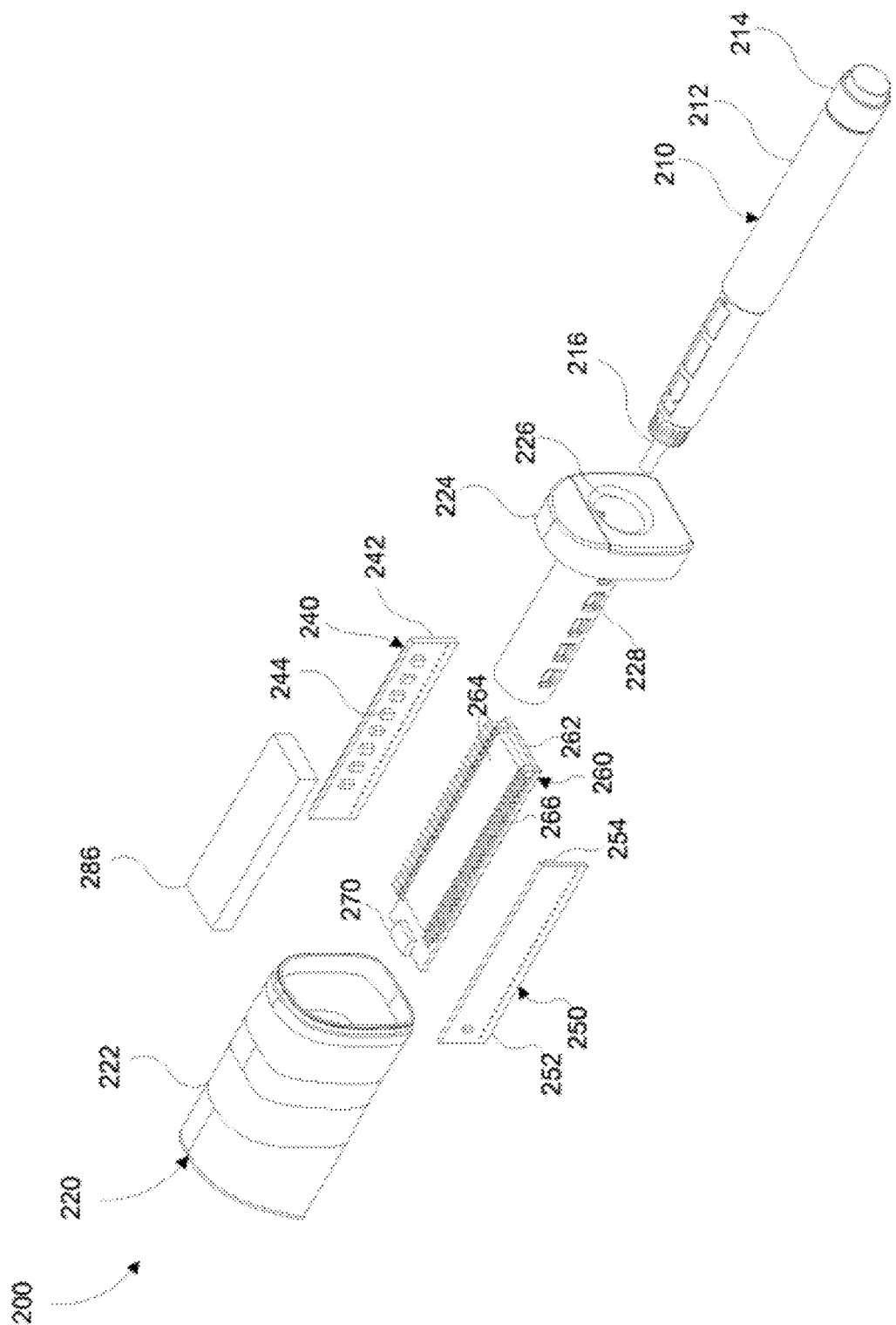
FIG. 3 is an exploded perspective view of the dose measurement system of FIG. 2 in accordance with some embodiments.
Figure 4:
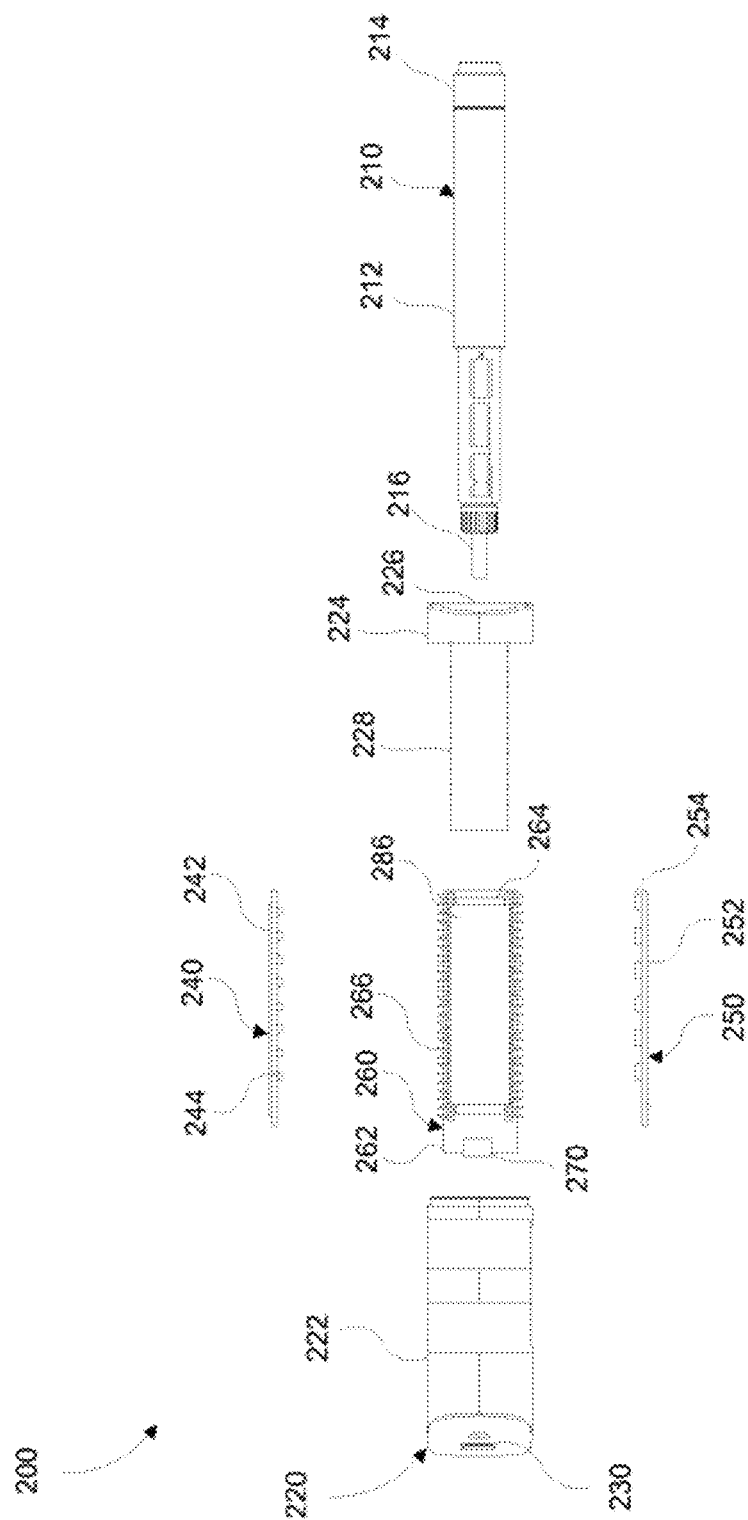
FIG. 4 is a top exploded top view of the dose measurement system of FIG. 2 in accordance with some embodiments.

Referring now to FIGS. 2-4, dose measurement system 200 may include a lighting module 240, a sensing module 250, a processing unit 260, a communications module 270, and a power source 286 according to some embodiments. Dose measurement system 200 may be configured to be removably coupleable to a drug delivery device 210 (also referred to herein as "an injection pen 210"). Drug delivery device 210 may be configured to deliver a predefined quantity of a drug (e.g., a dose) to a patient. Examples of drug delivery device 210 include insulin injection pens that may be used by a patient to self-administer insulin. As described herein, drug delivery device 210 may include a housing 212, an actuator 214, and an injector 216. Housing 212 may be relatively opaque, such that it only allows select wavelengths of electromagnetic radiation (e.g., infrared or microwave radiation) to be transmitted there through. Housing 212 defines an internal volume (e.g., reservoir) for storing a drug. Actuator 214 may include a plunger portion in fluid communication with the drug and configured to communicate a predefined quantity of drug to the patient. Actuator 214 may be configurable by, for example, the user, to dispense variable quantities of the drug. Injector 216 is configured to penetrate a user's skin for intramuscular, subcutaneous, and/or intravenous delivery of the drug.

Dose measurement system 200 includes a housing 220 that includes a top housing portion 222 (also referred to herein as "top housing 222") and a bottom housing portion 224 (also referred to herein as "bottom housing 224"). Top housing portion 222 and bottom housing portion 224 may be removably or fixedly coupled together by, for example, gluing, hot welding, and/or using a snap-fit mechanism, using a screw, or by any other suitable coupling means. Housing 220 may be made from a rigid, lightweight, and/or opaque material, including, but not limited to, polytetrafluoroethylene, high density polyethylene, polycarbonate, other plastics, acrylic, sheet metal, and any other suitable material or a combination thereof. Housing 220 also may be configured to shield the internal electronic components of dose measurement system 200 from environmental electromagnetic noise. For example, the housing may include an insulation structure (not shown) such as, for example, an aluminum lining or any other metal sheet or foil that can serve as an electromagnetic shield.

As shown in FIG. 3, top housing portion 222 defines an internal volume for substantially housing the lighting module 240, the sensing module 250, processing unit 260, communications module 270 and the power source 286 according to some embodiments. Bottom housing portion 224 includes defines a bore 226, shaped and sized to receive at least a portion of drug delivery device 210. For example, bore 226 may be shaped and sized to receive only the drug containing portion of housing 212 and injector 216. Bore 226 may be configured to receive drug delivery device 210 in a preferred orientation, such as a preferred radial orientation. In some embodiments, bore 226 is in close tolerance with the diameter of drug delivery device 210 to, for example, form a friction fit with drug delivery device 210. In some embodiments, bore 226 includes one or more notches, grooves, detents, any other snap-fit mechanism, or threads, for removably coupling drug delivery device 210 to the bottom housing 224. In some embodiments, bottom housing portion 224 includes one or more alignment features to allow drug delivery device 210 to be coupleable with dose measurement system 200 in a predetermined radial orientation.

In some embodiments, the bottom housing 224 includes one or more apertures 228 for receiving at least a portion of the plurality of light sources 244 of the lighting module 240, and/or sensors 254 of the sensing module 250. The apertures 228 may be configured to provide mechanical support for the light sources 244 and/or sensors 254, or may serve as an alignment mechanism for the lighting module 240 and/or sensing module 250.

As shown in FIG. 4, the top housing 222 includes an opening 230 for receiving at least a portion of communications module 270 such as, for example, a communication interface to provide wired communication with an external device, and/or an interface for charging the power source 286 according to some embodiments. In some embodiments, the top housing 222 also includes one or more features (e.g., recesses, apertures, cavities, etc.) for receiving a portion of drug delivery device 210 such as injector 216. In some embodiments, housing 220 also includes a detection mechanism (not shown) to detect if drug delivery device 210 has been coupled to dose measurement system 200. The detection mechanism may include, but is not limited to, a push switch, a motion sensor, a position sensor, an optical sensor, a piezoelectric sensor, an impedance sensor, or any other suitable sensor. Housing 220 may be relatively smooth and free of sharp edges. In some embodiments, housing 220 is shaped to resemble a pen cap that has a form factor that occupies minimal space (e.g., fitting in a user's pocket). In some embodiments, housing 220 also includes an attachment feature (e.g., a clip for attaching to a user's pocket or belt) and/or an ornamental feature. In some embodiments, dose measurement system 200 also serves as a replacement cap for drug delivery device 210.

Referring still to FIGS. 3 and 4, the plurality of light sources 244 (e.g., a plurality of LEDs or a single LED connected to a light pipe splitting emitted electromagnetic radiation into the plurality of light sources) of the lighting module 240 are mounted on, or otherwise disposed on, a printed circuit board (PCB) 242. The PCB 242 may be any standard PCB made by any commonly known process. In some embodiments, the plurality of light sources 244 is arranged in a straight line and equally spaced such that, when the portion of drug delivery device 210 that defines the internal volume of housing 212 holding the drug is coupled with dose measurement system 200, the light sources 244 illuminate the entire internal volume. In some embodiments, the light sources 244 are placed in any other configuration, including, but not limited to, a zig-zag configuration, an unequally spaced configuration, a staggered configuration, a configuration in which the light sources 244 are alternately disposed with the sensors 254, and/or any other configuration as described herein.

In some embodiments, the light sources 244 are configured to produce an electromagnetic radiation of a wavelength that is capable of penetrating through housing 212 of drug delivery device 210, the drug contained therein, and/or a portion of housing 220. For example, infrared radiation or microwave radiation can penetrate many of the plastic materials that are commonly used in manufacturing drug delivery devices (e.g., injection pens). In some embodiments, an electromagnetic radiation has a frequency that also penetrates through the internal components of drug delivery device 210 (e.g., the plunger portion of actuator 214). In some embodiments, each of the light sources 244 is configured to produce a wide angle beam of electromagnetic radiation (e.g., a plurality of wide angle LEDs or a single LED connected to a light pipe configured to produce a plurality of wide angle electromagnetic radiation beams). Said another way, the electromagnetic radiation cone of a single light source 244 may have a wide angle, and the electromagnetic radiation cones of adjacent light sources 244 may overlap. In some embodiments, the plurality of light sources 244 are configured to emit pulses of electromagnetic radiation (e.g., a series of less than 100 microsecond pulses).

The plurality of sensors 254 of the sensing module 250 are mounted on, or otherwise disposed on, a PCB 252. The PCB 252 may be any standard PCB made by any commonly known process. The plurality of sensors 254 may be any optical sensors (e.g., photodiodes) optically coupleable with the plurality of light sources 244 and configured to detect at least a portion of the electromagnetic radiation emitted by the plurality of light sources 244. The electromagnetic radiation may be transmitted radiation (e.g., transmitted through air, drug, and/or body of drug delivery device 210), refracted radiation (e.g., refracted by air, drug, and/or body of drug delivery device 210), reflected radiation (e.g., reflected from a wall of housing 220 or internally reflected from a wall of drug delivery device 210), and/or multi-directional refraction/reflection caused by a lensing effect of a curved surface of housing 212 and/or the drug reservoir. The transmitted, refracted, and/or reflected electromagnetic signal received by the plurality of sensors 254 may be used to create a signal signature (e.g., by processing unit 260). For example, the signal signature may then be associated with a reference signature to determine the dose remaining in drug delivery device 210. In some embodiments, the signal response of the sensors 254 may be used to measure usability metrics such as, for example, determining the presence of injector 216 of drug delivery device 210, and/or determining whether drug delivery device 210 is coupled/uncoupled to dose measurement system 200. In some embodiments, the sensors 254 are arranged in a substantially similar configuration to the light sources 244. In some embodiments, the number of sensors 254 is greater or less than the number of light sources 244. In some embodiments, the light sources 244 and sensors 254 are arranged such that each PCB 244, 254 includes a combination of light sources 244 and sensor 254 (e.g., arranged alternatively). In some embodiments, the light sources 244 and/or sensors 254 are arranged in an inclined orientation.

Processing unit 260 may include a PCB 262 and a processor 264. The PCB 262 may be any standard PCB made by any commonly known process and may include amplifiers, transistors and/or any other electronic circuitry as necessary. The processor 264 may be any processor, including, but not limited to, a microprocessor, a microcontroller, a PLC, an ASIC chip, an ARM chip, an ADC, or any other suitable processor. Processing unit 260 may be coupled to the lighting module 240 and the sensing module 250 using electronic couplings 266, such that the lighting module 240 and the sensing module 250 are oriented perpendicular to processing unit 260 and parallel to each other. In some embodiments, processing unit 260 includes an onboard memory for at least temporarily storing a signal signature, a reference signature database, dose information, user health data (e.g., blood glucose level), device location data (e.g., from a GPS receiver optionally included in dose measurement system 200 or from another GPS-enabled device that is communicatively coupled with the system 200 such as a blood glucose meter or a cellular phone), and any other data as might be useful for a patient to manage their health. In some embodiments, processing unit 260 includes an RFID chip configured to store information and allow an NFC device to read the information stored therein. Processing unit 260 may be configurable to control the operation of dose measurement system 200, for example, activation and timing of the light sources 244, and/or reading and processing of electromagnetic radiation data from the sensors 254. For example, processing unit 260 may be configured to compare electromagnetic radiation signal signature obtained from the plurality of sensors 254 and associate it with the reference signature database to determine the quantity of dose remaining in drug delivery device 210 or the position of actuator 214 (e.g., a plunger) of drug delivery device 210.

In some embodiments, processing unit 260 is configured to correct the signal signature for background noise. For example, processing unit 260 may be configured to operate the sensing module 250 to detect a background signature with the lighting module in dark state, i.e., each of the plurality of light sources 244 switched off. The background signature may be associated with the signal signature to correct for background noise. In some embodiments, processing unit 260 also includes electronic signal filtering algorithms, including, but not limited to, a Fourier transform, a low pass filter, a band pass filter, a high pass filter, a Bessel filter, and/or any other digital filter to reduce noise and increase signal quality. Processing unit 260 also may be configured to obtain reference signatures by storing the electromagnetic radiation signal detected by the sensing module 250 for a range of dose volumes in a representative drug delivery device 210, including, but not limited to, full, empty, and/or a series of intervals there between (e.g., every unit of dose dispensed from the drug delivery device and/or every 170 micrometer displacement of a plunger portion of actuator 214 included in drug delivery device 210).

In some embodiments, processing unit 260 is configured to include probabilistic matching algorithms that can be used to associate the signal signature with the reference signature to determine a volume of liquid in drug delivery device 210. Processing unit 260 also may be configured to control and operate communications module 270. In some embodiments, processing unit 260 is configured to operate the system in a power efficient manner. For example, processing unit 260 may turn off at least some of the electronics powering the light sources 244 (e.g., an operational amplifier) when not needed. Processing unit 260 may pulse the light sources 244 for a short period at high current to, for example, save power and/or increase signal-to-noise ratio. Processing unit 260 also may be configured to periodically activate communications module 270, including, but not limited to, a predetermined number of times per day (e.g., ten times) and/or when dose measurement system 200 is attached to drug delivery device 210. Processing unit 260 also may be configured to deactivate communications module 270 when it is not needed. In some embodiments, processing unit 260 also includes a global positioning/navigation system (e.g., GPS) to, for example, determine a current location of dose measurement system 200.

Communications module 270 may be configured to communicate data to the user and/or an external device, for example, a smart phone application, a local computer, and/or a remote server. The communicated data may include, but is not limited to, initial system activation, system ON/OFF, coupling/uncoupling of a drug delivery device, dose remaining, dose history, time, system and/or drug temperature, system location (e.g., GPS), drug delivery device 210 data, drug expiration data, velocity at which drug is delivered, device collisions, device power remaining, step count, tampering with the system, and/or any other user health information or other usable data. In some embodiments, communications module 270 also is configured to receive data, for example, new calibration data, firmware updates, user health information (e.g., blood glucose, diet, exercise, and/or dose information), and/or any other information input by the user and/or communicated from an external device. Communications module 270 may include conventional electronics for data communication and may use a standard communication protocol, including, but not limited to, Wi-Fi, Bluetooth®, low powered Blue-Tooth®, ZigBee, USB, firewire, and/or NFC (e.g., infrared). In some embodiments, communications module 270 is configured to periodically connect (e.g., ten times per day) to an external device (e.g., a smart phone) to log any dose data stored in the onboard memory. In some embodiments, communications module 270 is activated/deactivated on demand by the user.

Figure 5:
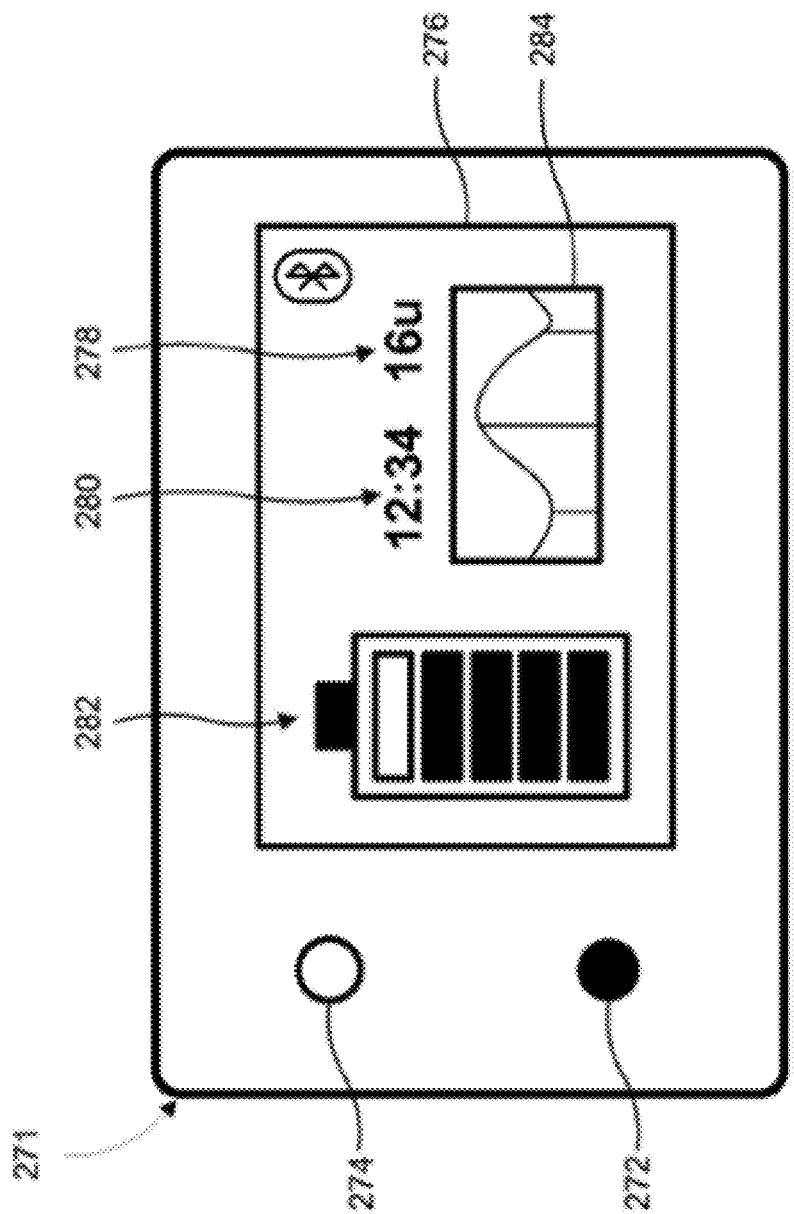
FIG. 5 is a schematic illustration of a communications interface that may be included in the dose measurement system of FIG. 2 in accordance with some embodiments.

Referring now also to FIG. 5, communications module 270 may include a communication interface 271 located on an external surface of the housing 210 of dose measurement system 200 for communicating with the user according to some embodiments. Communication interface 271 may include a switch 272 (e.g., a power switch, a reset button, and/or another communication switch) to manually initiate communication with an external device (e.g., activate Bluetooth®). In some embodiments, the communications interface 271 also includes an indicator 274 such as a light source (e.g., an LED) to indicate to the user, for example, if dose measurement system 200 is ON/OFF or if communication module 270 is active. In some embodiments, communication interface 271 includes a display 276 for visual communication of information to the user, including, but not limiting to, a dose remaining 278 in drug delivery device 210, a current time 280, system power remaining 282, dose history 284 (e.g., average dose usage, time last dose taken, etc.), and/or a wireless connectivity status. In some embodiments, the communications interface 271 includes an input component (e.g., an alphanumeric keypad and/or a touch screen) to allow a user to input information (e.g., food intake, exercise data, etc.) into dose measurement system 200. In some embodiments, communications module 270 includes a speaker for providing audible alerts or messages to the user (e.g., dose reminders and/or reinforcement messages) and/or a microphone for receiving audio input from the user. In some embodiments, communications module 270 includes means for tactile alerts (e.g., a vibration mechanism). In some embodiments, communications module 270 communicates other information pertaining to user health (e.g., steps taken, calories burned, blood glucose levels, etc.).

The power source 286 may be any power source that can be used to power dose measurement system 200. In some embodiments, the power source 286 includes a disposable battery. In some embodiments, the power source 286 includes a rechargeable battery (e.g., a NiCad battery, a Li-ion battery, a Li-polymer battery, or any other battery that has a small form factor, such as the types used in cell phones) and/or does not to be charged frequently (e.g., once per month). In some embodiments, the power source 286 is charged using an external power source (e.g., though a power socket located on housing 220 or through a communication interface of communications module 270, such as a wired USB interface or via wireless charging). In some embodiments, the power source 286 is charged using solar energy and includes solar panels. In some embodiments, the power source 286 is charged using kinetic energy and includes mechanical energy transducers.

As described above, the plurality of sensors 254 of the sensing module 250 are configured to receive at least one of transmitted radiation, refracted radiation (e.g., refracted by air, liquid drug, housing 212 of drug delivery device 210), reflected radiation (e.g., reflected from a wall of housing 220 or internally reflected from a wall of the internal volume of drug delivery device 210), and multi-directional reflection/refraction caused by a lensing effect of a curved surface of housing 212 of drug delivery device 210.

Figure 6:
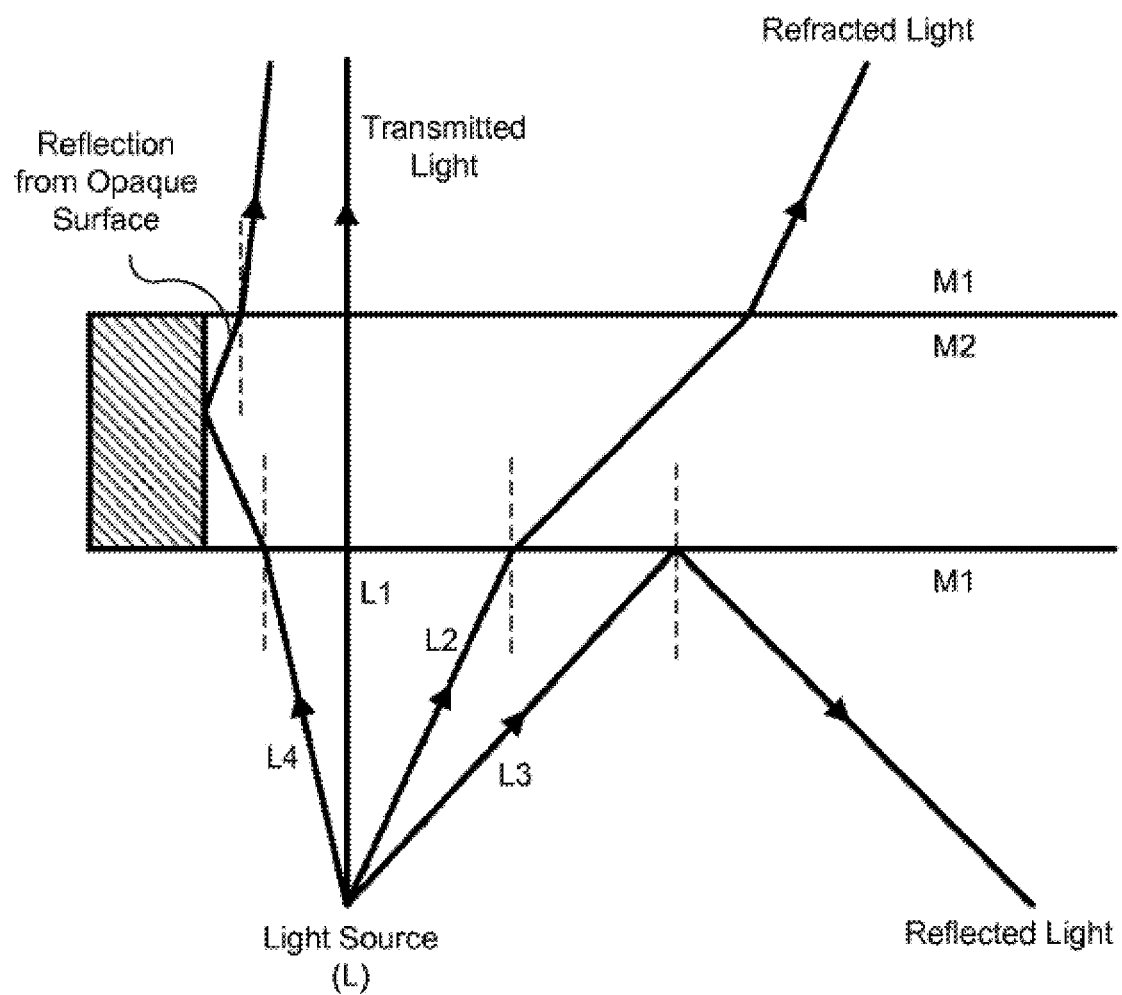
FIG. 6 is a schematic ray diagram of different modes of light transmission between a first medium and a second medium in accordance with some embodiments.

Referring now to FIG. 6, a light source L (e.g., a wide angle light source) may produce a plurality of light rays emanating and diverging away from the light source according to some embodiments. The light source L is present in a first medium M1 (e.g., air) having a first refractive index n1. A second medium M2 (e.g., liquid drug) having a second refractive index n2, is bordered by the first medium M1 on both sides. The second refractive index n2 is greater than the first refractive index n1 (i.e., n2>n1). The second medium M2 also includes an opaque surface (e.g., a sidewall).

A first light ray L1 emitted by the light source L is incident on the interface of the first medium M1 and the second medium M2 at a first angle of degrees. This light ray does not bend as it penetrates through the second medium M2 and transmits back into the first medium M1 at the original angle of incidence (i.e., transmitted light).

A second light ray L2 is incident on the interface of the first medium M1 and the second medium M2 at a second angle greater than zero degrees. The second light ray L2 bends or refracts as it penetrates the second medium M2, and then bends again to its original angle of incidence as it reenters the first medium M1, parallel to but offset from the emitted ray L2 (i.e., refracted light).

A third light ray L3 is incident on the interface of the first medium M1 and the second medium M2 at a third angle greater than the second angle. At this angle of incidence, the light ray L3 does not penetrate into the second medium M2 but is reflected back into the first medium M1, such that angle of reflection is equal to the angle of incidence (i.e., reflected light).

A fourth light ray L4 is incident on the interface of the first medium M1 and the second medium M2 at a fourth angle less than the third angle, such that the light ray L4 refracts in the second medium M2, but is now incident on the opaque surface included in the second medium M2 (i.e., reflection from an opaque surface). At least a portion of the light ray L4 is reflected back into the second medium M2, which then reenters back into the first medium M1 at a fifth angle, such that the fifth angle is not equal to the fourth angle.

As described herein, the electromagnetic radiation signal received by the plurality of sensors 254 of the sensing module 250 may include a combination of the transmitted, refracted and reflected portions of the electromagnetic radiation. A unique signal signature is produced by the combination of the portions of the electromagnetic radiation at different dose volumes remaining, and/or the actuator 216 position of drug delivery device 210. This signal signature may be compared with a reference signal signature database (also referred to herein as a "calibration curve") to obtain the volume of dose remaining in drug delivery device 210, as described in further detail herein.

Figure 7:
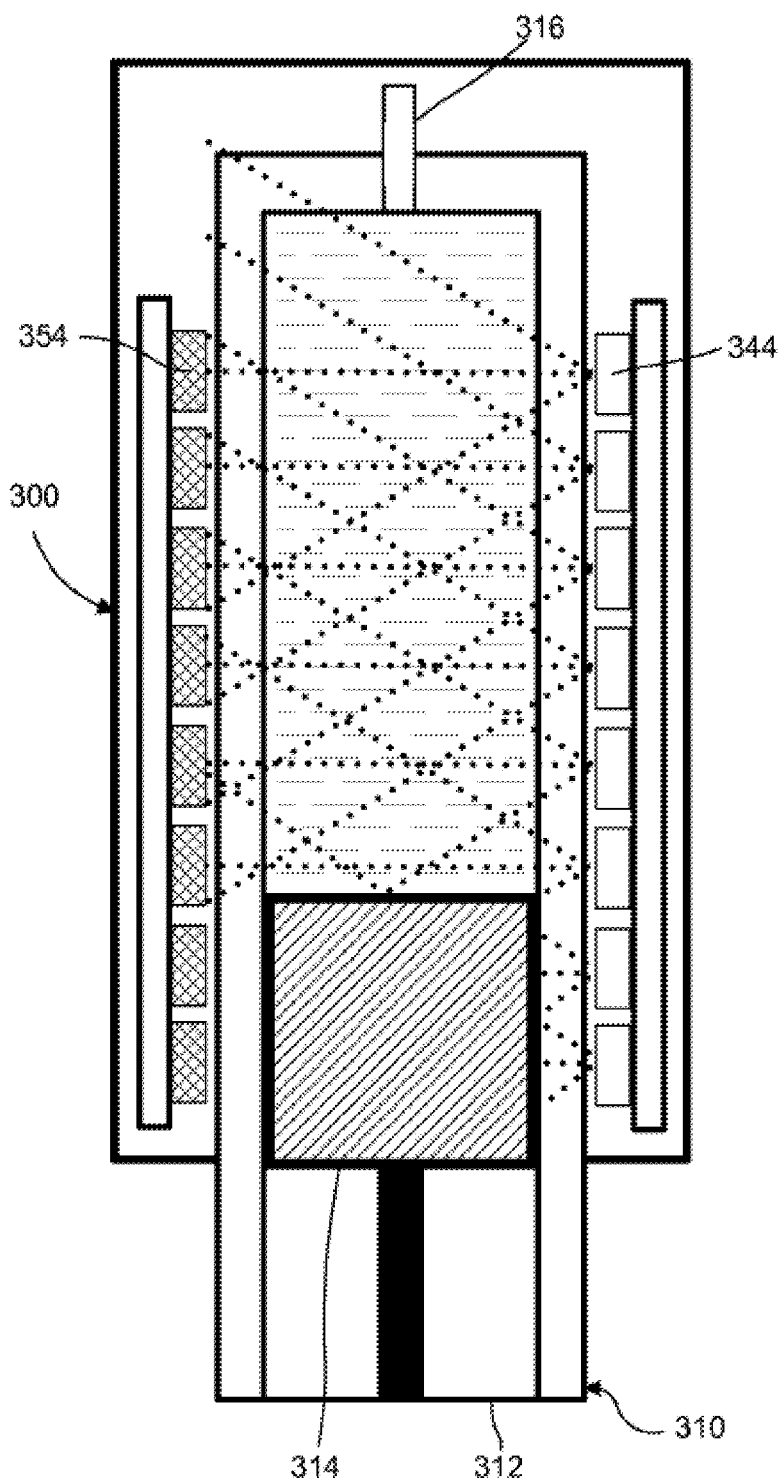
FIG. 7 is a cross-sectional view of a dose measurement system in accordance with some embodiments.

Referring now to FIGS. 7-10, various configurations of the light sources and the sensors are shown and described according to some embodiments. While the transmitted and reflected portion of the electromagnetic radiation emitted by the light sources is shown, the refractive portion is not shown for clarity. As shown in FIG. 7, a dose measurement system 300 includes a plurality of light sources 344 and a plurality of sensors 354. A drug delivery device 310 is coupled to the dose measurement system 300 according to some embodiments. The drug delivery device 310 includes a housing 312 and an actuator 314 that collectively define an internal volume (e.g., a reservoir) for containing a drug. The drug delivery device 310 also includes an injector 316 for administering the drug to a patient. The dose measurement system 300 is configured such that the plurality of light sources 344 are disposed on a first side of the housing oriented towards the drug delivery device 310 and the plurality of sensors 354 are disposed on a second side of the housing such that each of the plurality of sensors 354 is substantially opposite to, and in optical communication with, at least one of the plurality of light sources 344. In some embodiments, the plurality of light sources 344 and/or the plurality of sensors 354 is disposed in a substantially linear relationship (e.g., a straight line) with respect to each other. Each of the plurality of sensors 354 receive a combination of transmitted, refracted, and/or reflected electromagnetic radiation emitted by the plurality of light sources 344. The reflection portion of the electromagnetic radiation may be reflected from a plunger portion of the actuator 314, and/or reflected from a housing of the dose measurement system 300 or the housing 312 of the drug delivery device 310. The refraction may be from the housing 312 and/or from the liquid drug disposed in the drug delivery device 310. The combination of the transmitted, reflected and refracted portions of the electromagnetic radiation detected by each of the plurality of sensors yields a unique signal signature for a range of dose volumes remaining in the drug delivery device 310.

Figure 8:
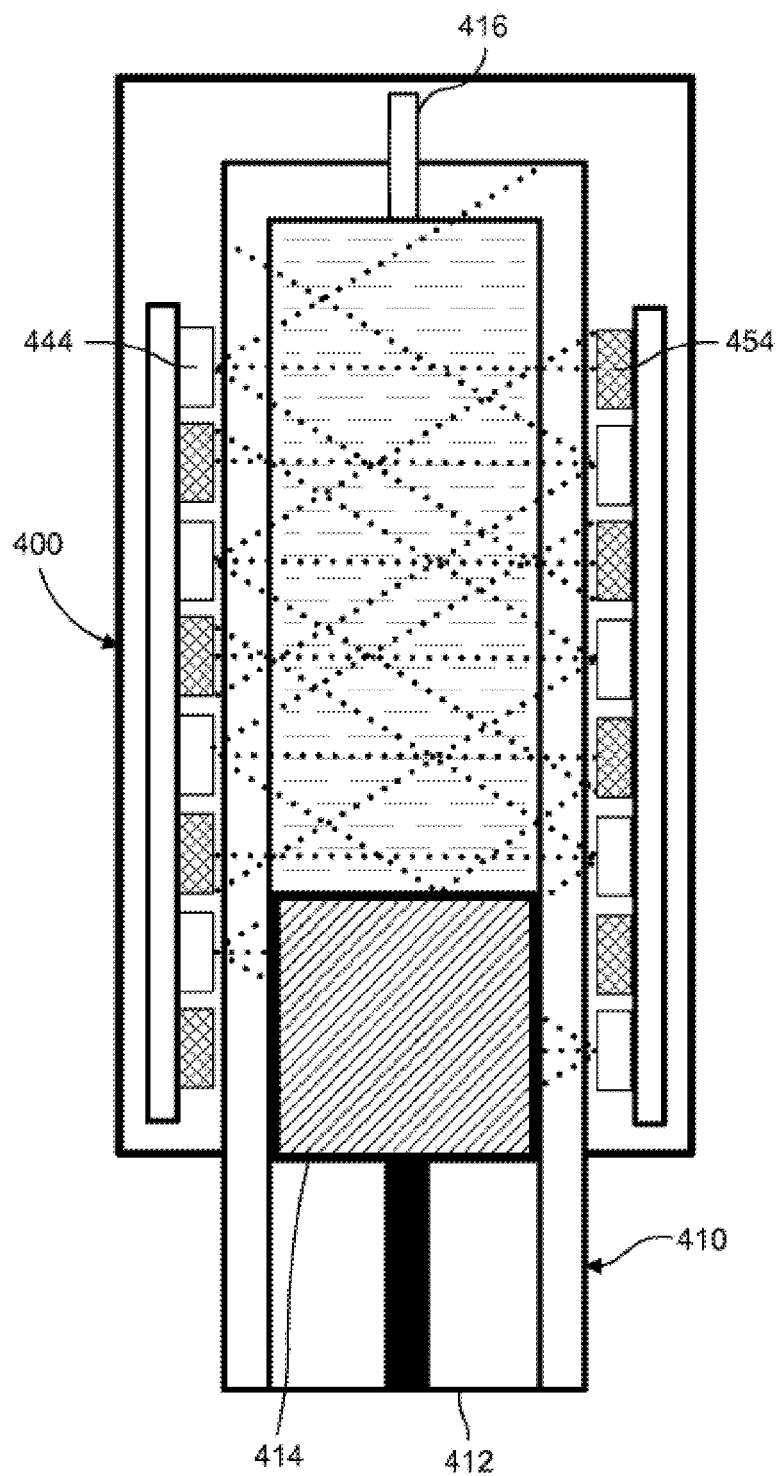
FIG. 8 is a cross-sectional view of a dose measurement system in accordance with some embodiments.

In some embodiments, a plurality of light sources and a plurality of sensors are alternately disposed on both sides of a drug delivery device. As shown in FIG. 8, a dose measurement system 400 may include a plurality of light sources 444 and a plurality of sensors 454 according to some embodiments. The drug delivery device 410 includes a housing 412 and an actuator 414 that collectively define an internal volume (e.g., a reservoir) for containing a drug. The drug delivery device 410 also includes an injector 416 for communicating the drug to a patient. The dose measurement system 400 is configured such that the plurality of light sources 444 and the plurality of sensors 454 are disposed on both sides of the drug delivery device. In other words, each side of the drug delivery device 410 has a plurality of light sources 444 and a plurality of sensors 454. This may be advantageous as emission and detection of electromagnetic radiation is now performed from both sides of the drug delivery device 410, which can, for example, remove any biases.

Figure 9:
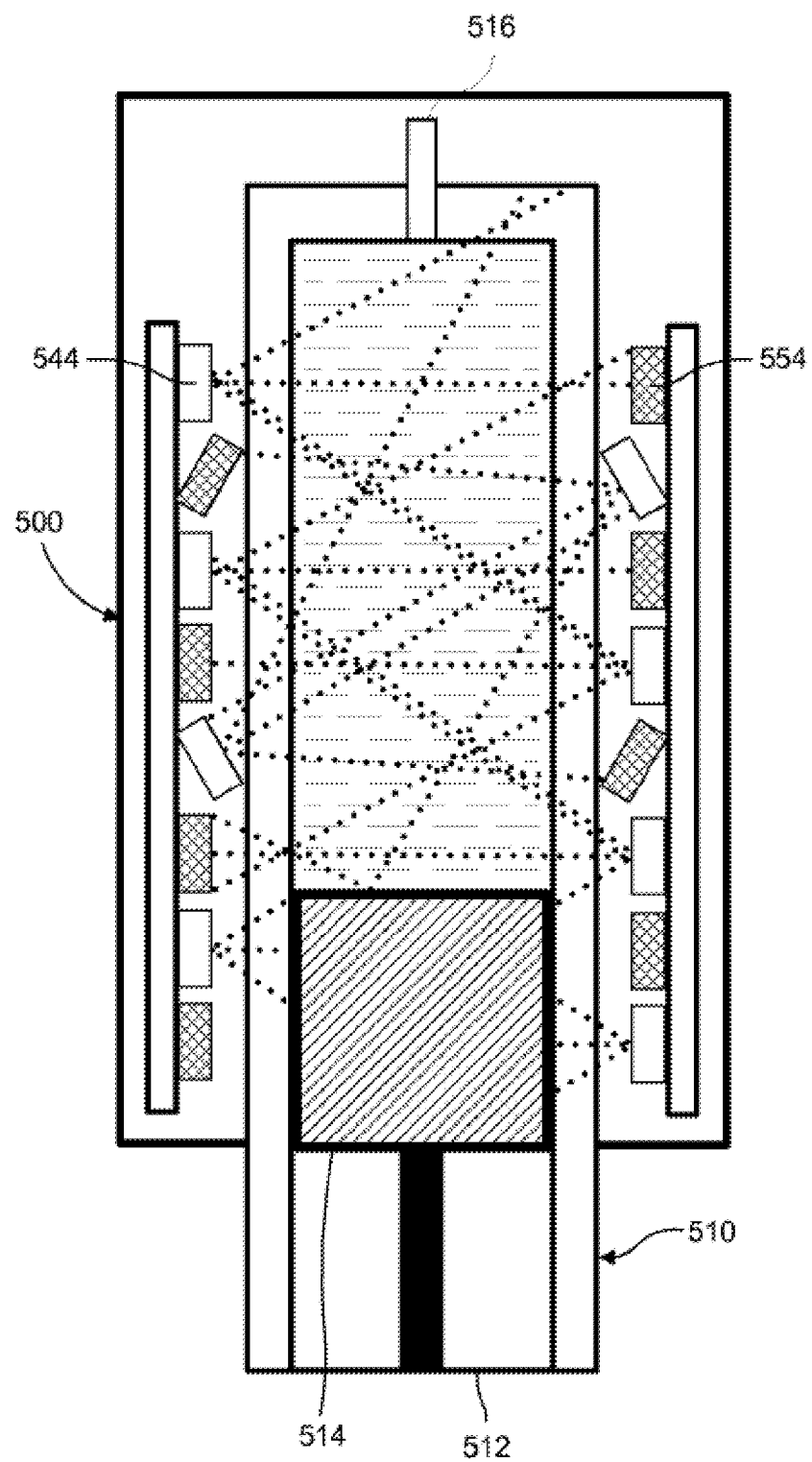
FIG. 9 is a cross-sectional view of a dose measurement system in accordance with some embodiments.

In some embodiments, at least a portion of the plurality of light sources and/or the plurality of sensors is arranged in an angular orientation. As shown in FIG. 9, a dose measurement system 500 includes a plurality of light sources 544 and a plurality of sensors 554 according to some embodiments. The drug delivery device 510 includes a housing 512 and an actuator 514 that collectively define an internal volume (e.g., a reservoir) for containing a drug. The drug delivery device 510 also includes an injector 516 for communicating the drug to a patient. The dose measurement system 500 is configured such that the plurality of light sources 544 and the plurality of sensors 554 are disposed on both side of the drug delivery device 510 and have an angular orientation with respect to a longitudinal axis of the dose measurement system 500 and drug delivery device 510. This orientation may ensure that the electromagnetic radiation emitted by the plurality of light sources 544 is incident on a larger portion of the drug delivery device 510 than is achievable with the light sources 544 oriented in a straight line. Similarly, the plurality of sensors 554 also may detect a greater portion of the electromagnetic radiation. This can, for example, result in higher resolution of the sensors 554, and/or reduce the quantity of light sources 544 and/or sensors 554 required to achieve the desired resolution.

In some embodiments, wider angle light sources (e.g., wide angle LEDs or a single LED connected to a light pipe splitting emitted electromagnetic radiation into a plurality of wide angle beams), for example, also may be used ensure that the electromagnetic radiation emitted by the plurality of light sources 544 is incident on a larger portion of the drug delivery device 510 than is achievable with a narrower beam light sources 544. In other words, with a wider beam emitted by the light sources 544, a higher proportion of the overall drug delivery device 510 (or of the drug reservoir) is in optical communication with the light sources 544. Since a higher proportion of the delivery device 510 is in optical communication with the light sources 544, a broader spectrum of electromagnetic radiation being transmitted, reflected and/or refracted through the drug delivery device can increase the signal strength detectable by the plurality of sensors 554. Said other way, variability in the signal signatures (as opposed to increased intensity of light incident on the sensor) increases with the broadening of the beam of light incident on the delivery device, therefore increasing the resolution of the dose measurement system 500. For example, wider angles may increase ability to distinguish states of the drug delivery device, even though the overall intensity of light may be lower. This is because distinguishing states is more about optimizing how the intensity of light changes from state to state than it is about the absolute intensity of light.

Figure 10:
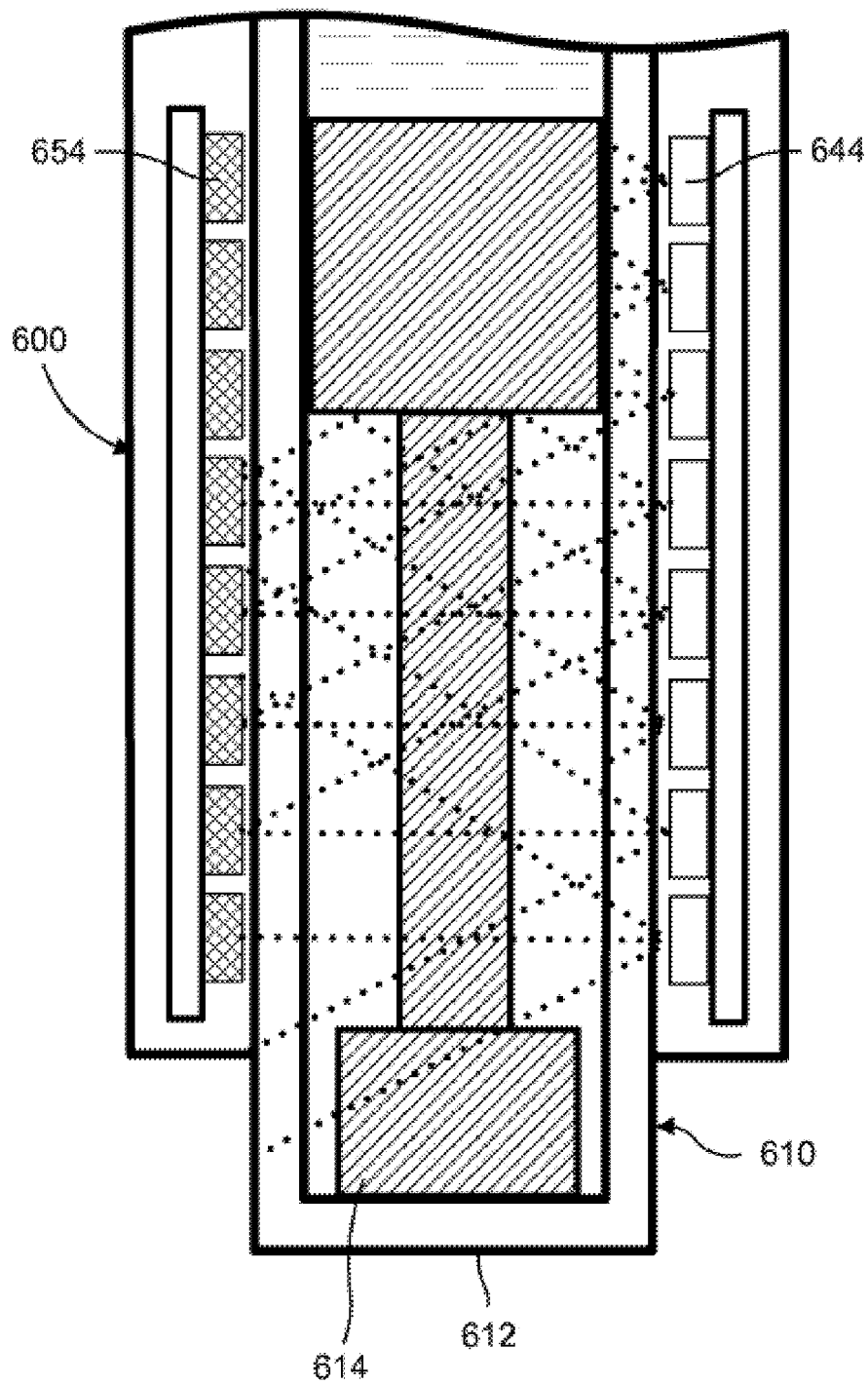
FIG. 10 is a side cross-sectional view of a dose measurement system in accordance with some embodiments.

In some embodiments, a dose measurement system is configured to detect a signal signature from a location of an actuator of a drug delivery device, which may be used to estimate the dose remaining in the drug delivery device. As shown in FIG. 10, a dose measurement system 600 includes a plurality of light sources 644 and a plurality of sensors 654 according to some embodiments. A drug delivery device 610 is coupled to the dose measurement system 600. The drug delivery device 610 includes a housing 612 and an actuator 614 that collectively define an interior volume (e.g. a reservoir) for containing a drug. The dose measurement system 600 is disposed generally about the actuator 614 portion of the drug delivery device 610 as opposed to the dose measurement systems 300, 400 and 500 being disposed generally around the drug reservoir as shown in FIGS. 7-9. The plurality of light sources 644 and sensors 654 are configured and arranged in a substantially similar way as described above with reference to FIG. 7. Electromagnetic radiation emitted by the plurality of light sources 644 may be transmitted unblocked by the actuator 614, blocked by a plunger portion of the actuator 614, reflected by a body or the plunger portion of the actuator 614 and/or reflected/refracted by the housing the drug delivery device 610. The combination of the transmitted, reflected and refracted portions of the electromagnetic radiation detected by the plurality of sensors 654 are then used to generate a signal signature at a given position of the actuator 614. Displacement of the actuator 614 from a first position to a second position changes the transmission, reflection and refraction pattern of the electromagnetic radiation detected by the sensors 654, creating a unique signal signature at each position of the actuator 614. This signature may be correlated to the dose volume remaining in the drug delivery device 610 (e.g., by association with a reference signature).

Figure 11A:
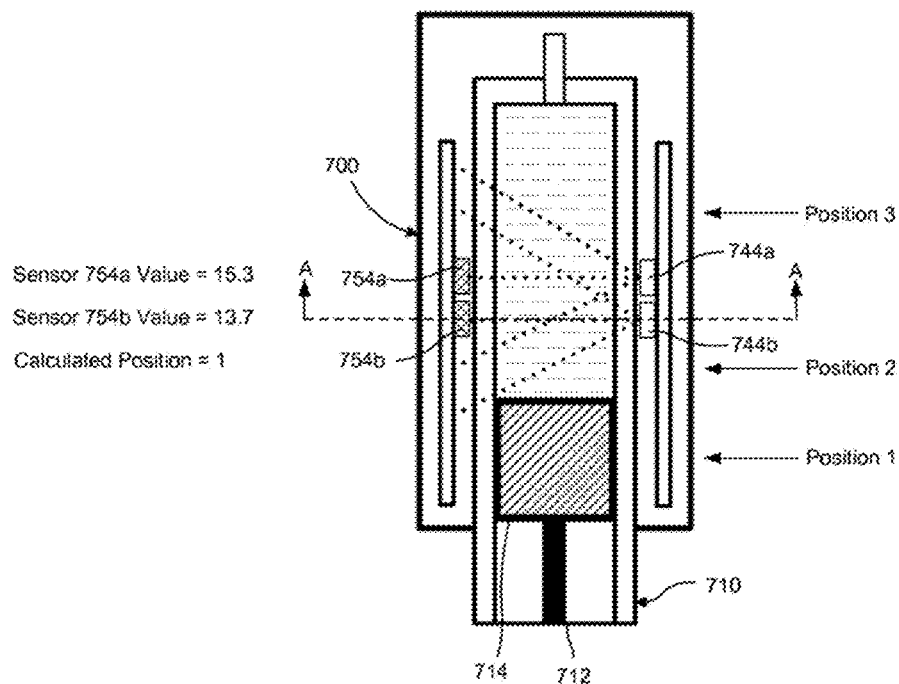
FIGS. 11A-11C are cross-sectional views of a dose measurement system in a first, second, and third configuration, respectively, in accordance with some embodiments.
Figure 11B:
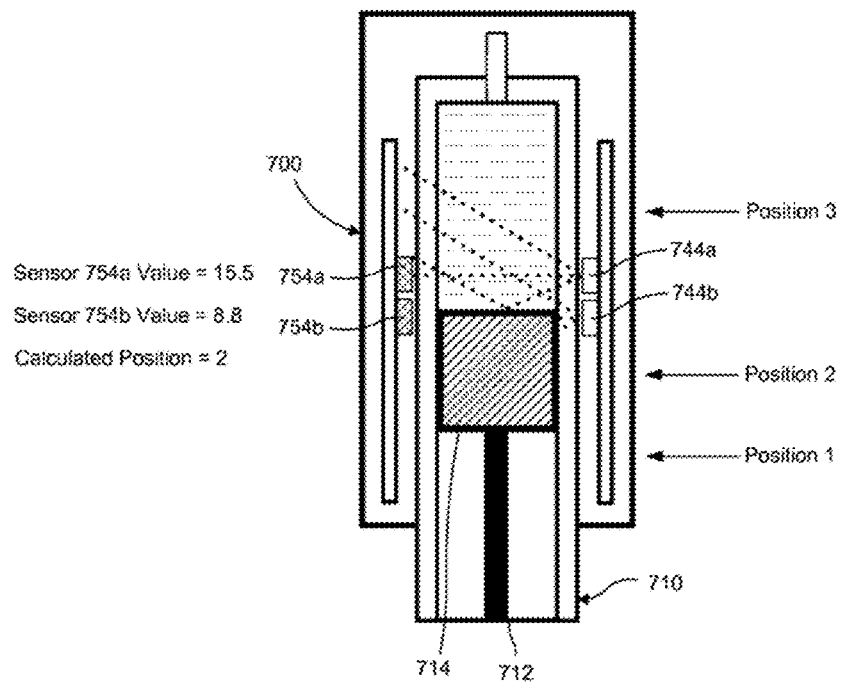
Figure 11C:
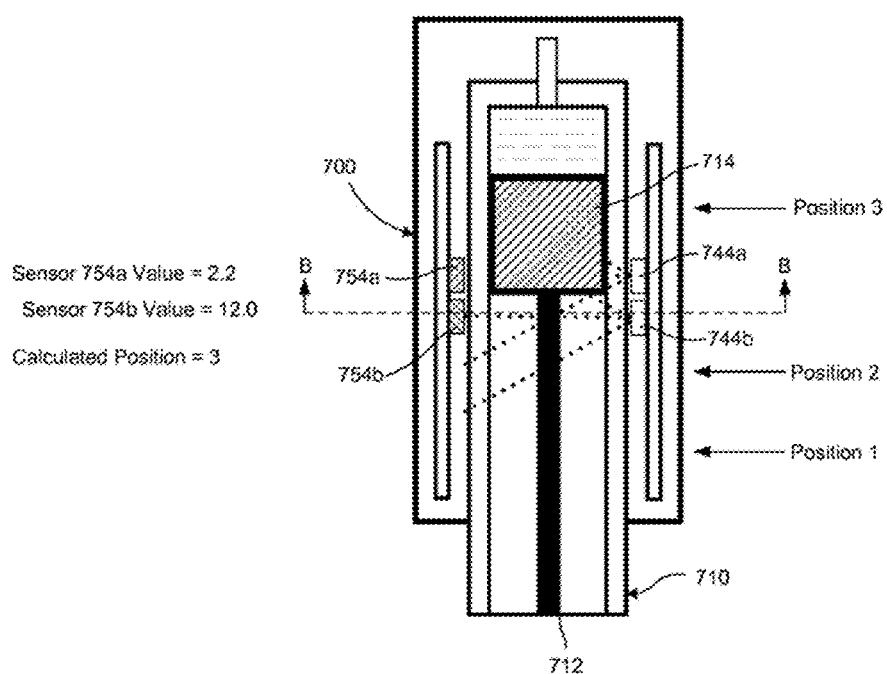

Referring now to FIGS. 11A-11C, each sensor of the plurality of sensors of a dose measurement system may detect electromagnetic radiation emitted by at least a portion of the plurality of light sources, and the detected electromagnetic radiation may be a combination of transmitted reflected and refracted electromagnetic radiation. As shown, the dose measurement system 700 includes two light sources 744a and 744b, and two sensors 754a and 754b for clarity. The dose measurement system 700 is coupled to a drug delivery device 710 which includes a housing 712 and an actuator 714 that collectively define an internal volume (e.g., a reservoir) for containing a liquid drug. The drug reservoir and at least a plunger portion of actuator 714 are disposed substantially inside the dose measurement system 700 between the light sources 744a, 744b and sensors 754a, 754b.

As shown in FIG. 11A, the plunger portion of actuator 714 is in a first position ("position 1") such that the plunger portion is not in the line of sight of light sources 744a and 744b and sensors 754a and 754b according to some embodiments. When electromagnetic radiation is emitted by the light sources 744a and 744b towards drug delivery device 710, a significant portion of the electromagnetic radiation is detected by the sensors 754a and 754b in position 1. The electromagnetic radiation may include transmitted radiation, reflected radiation (reflected by, e.g., housing 712 of drug delivery device 710), and refracted radiation (refracted by, e.g., the liquid drug and/or housing 712), and multi-direction reflected/refracted radiation (caused by, e.g., a curved surface of housing 712 of drug delivery device 710) as described in more detail below. As shown in this example, sensor 754a value is 15.3 and sensor 754b value is 13.7, which indicates that a significant portion of the electromagnetic radiation is detected by the sensors 754a and 754b.

As shown in FIG. 11B, actuator 714 is displaced to a second position ("position 2") such that the plunger portion partially blocks the line of sight between light source 744b and sensor 754b according to some embodiments. In position 2, a significant portion of the electromagnetic radiation emitted by light source 744b is blocked from reaching sensor 754b by actuator 714, but at least a portion of the electromagnetic radiation emitted by light source 744a can still reach sensor 754b along with any multi-directional reflected/refracted electromagnetic radiation. Furthermore, sensor 754a can receive refracted electromagnetic radiation from sensor 744b and transmitted, refracted radiation from sensor 744a. Sensor 754a also receives electromagnetic radiation reflected by a surface of the plunger that at least partially defines the drug reservoir. Therefore, at position 2 sensor 754a detects an electromagnetic radiation value of 15.5 (greater than at position 1), and sensor 754b detects an electromagnetic radiation value of 8.8 (less than at position 1). The unique values measured at position 2 can serve as the signal signature values for position 2.

As shown in FIG. 11C, the plunger portion of actuator 714 is in a third position ("position 3") such that the plunger portion of actuator 714 completely blocks the line of sight of the sensor 754a from the electromagnetic radiation emitted by light source 744a, such that substantially no transmitted and or reflected radiation from light source 744a can reach the sensor 754a according to some embodiments. A portion of the transmitted electromagnetic radiation emitted by light source 744b is also blocked by at least a portion of actuator 714, from reaching sensor 754b. Both the sensors 754a and 754b can still receive at least a portion of the reflected and refracted portions of the electromagnetic radiation emitted by any of the light sources 744a and/or 744b. Therefore, at position 3 the sensor 754a detects an electromagnetic radiation value of 2.2 (less than at positions 1 and 2), and sensor 754b detects an electromagnetic radiation value of 12.0 (less than at position 1, but greater than at position 2). The unique values measured at position 3 may serve as the signal signature values for position 3.

Figure 12:
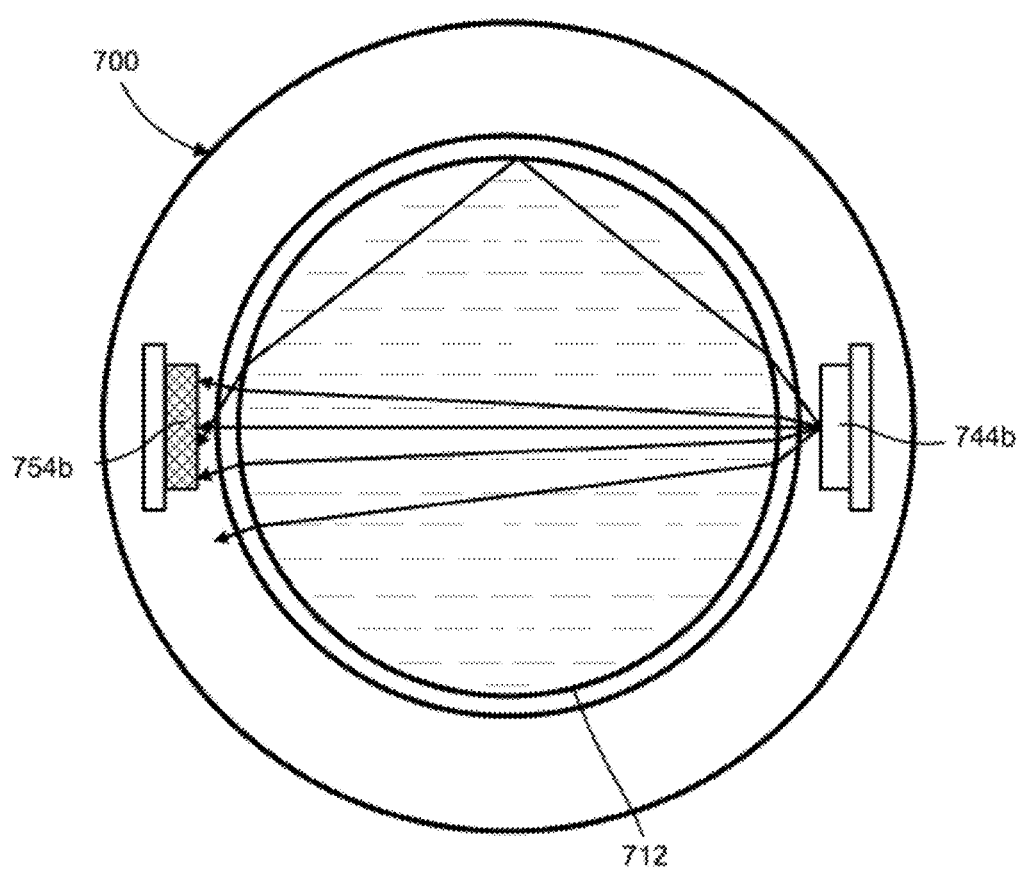
FIG. 12 is a cross-sectional view of the dose measurement system of FIG. 11A, taken along line A-A, in accordance with some embodiments.

Referring now to FIG. 12, a cross-section of the dose measurement system 700 taken along line AA in FIG. 11A illustrates the lensing effect caused by the curvature of the drug reservoir according to some embodiments. As shown, a light ray emitted at a zero degree angle by light source 744b is transmitted without bending towards sensor 754b. Two more light rays emitted by light source 744b, at an angle away from the transmitted ray, are caused to refract (i.e., bend) toward the transmitted ray as they enter the drug reservoir because the liquid drug has a higher refractive index than air. This phenomenon is referred to herein as "a lensing effect," which can result in focusing of the light rays toward sensor 754b. A fourth ray is emitted at an angle further away from the transmitted ray such that it refracts at the air/drug interface, and then is further reflected by an internal surface of housing 712 of the drug delivery system 710 such that it is incident on sensor 754b. A fifth ray is emitted at an angle, such that even after refraction it is not incident on sensor 754b. As described above, the combination of these rays yields a detected electromagnetic radiation value of 15.3 by sensor 754a and 13.7 by sensor 754b. These unique values measured at position 1 may serve as the signal signature values for position 1.

Figure 13:
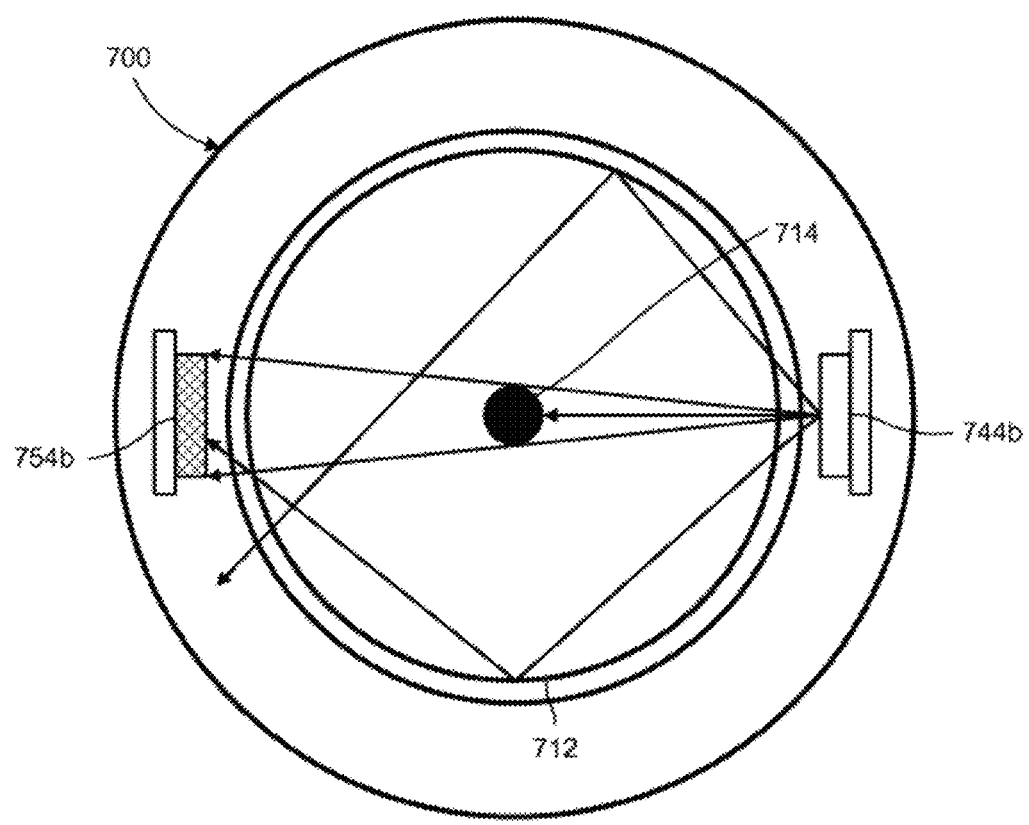
FIG. 13 is a cross-sectional view of the dose measurement system of FIG. 11C, taken along line B-B, in accordance with some embodiments.

Referring now to FIG. 13, a cross-section of the dose measurement system 700 taken along line BB in FIG. 11C illustrates effects of actuator 714 on the transmission of light according to some embodiments. As shown, a light ray emitted at a zero degree angle by light source 744b is blocked by a portion of actuator 714. Two more light rays emitted by light source 744b, at an angle away from the transmitted ray, pass underacted (refraction through the housing is ignored) through the portion of housing 712 of drug delivery device 710 (i.e., no drug exists in this portion of device 710) and are incident on sensor 754b. A fourth ray is emitted by light source 744b at an angle, such that it is internally reflected by housing 712 and is incident on sensor 754b, while a fifth ray is internally reflected by housing 712 but is not incident on sensor 754b. The combination of these rays yields a detected electromagnetic radiation value of 2.2 by sensor 754a and 12.0 by sensor 754b. These unique values measured at position 3 can serve as the signal signature values for position 3. It is to be noted that although the line of sight of sensor 754a is completely blocked from light source 744a, reflected and refracted portions of the electromagnetic radiation still contribute to generation of a positive value.

Although the sensor values for particular positions are described as being absolute values, individual sensor values relative to other sensor values may be used to infer and/or determine a volume of liquid remaining in the drug reservoir. For example, if sensor 754a has a particular value that is different from sensor 754b value by a certain amount or a certain percentage, it may be indicative of a position/drug volume remaining in a drug delivery device. Furthermore, a sensor value relative to two or more other sensor values may be used to generate a calibration curve of a drug delivery device.

Figure 14:
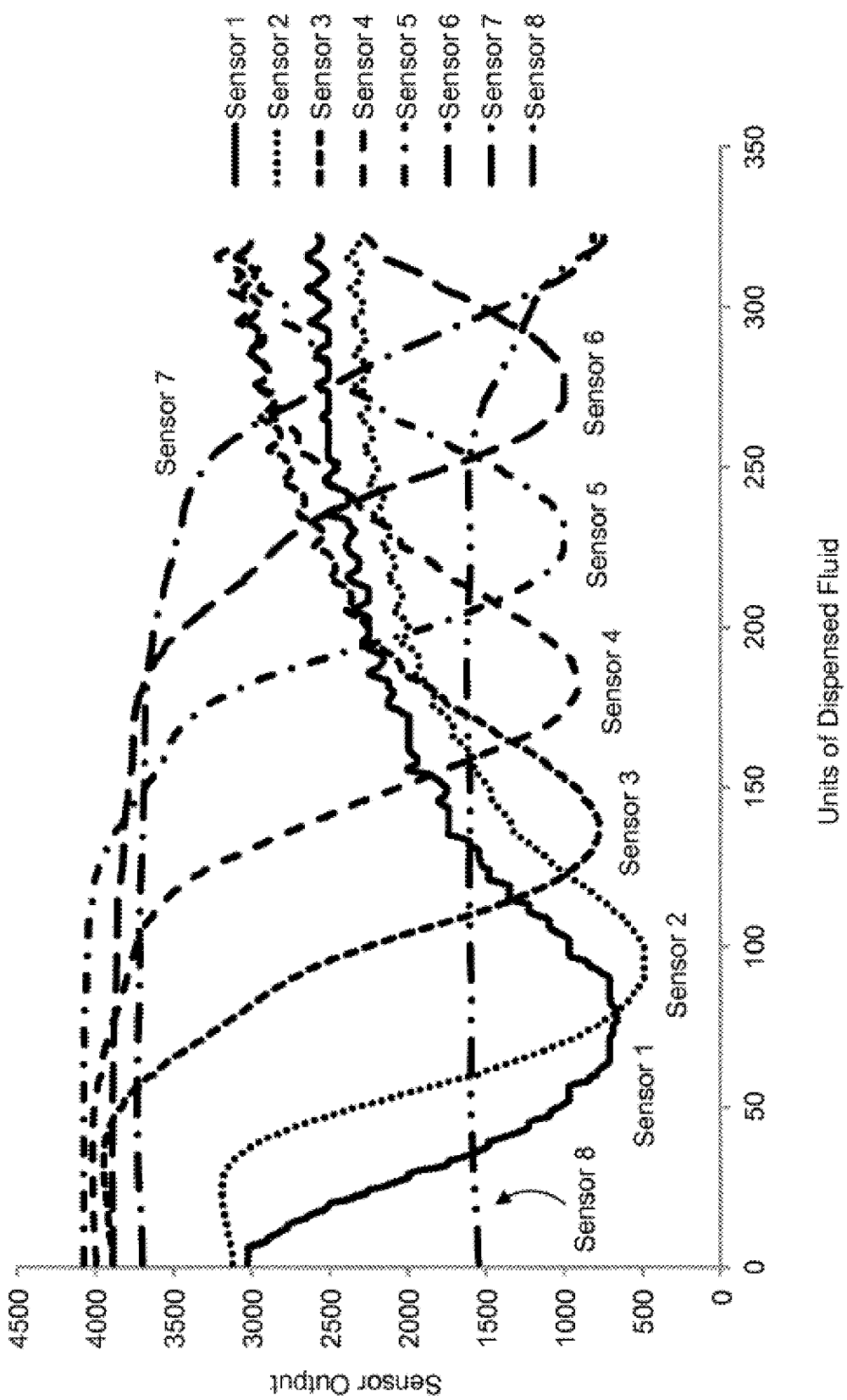
FIG. 14 is a graph showing reference signature signals of sensors of a dose measurement system in accordance with some embodiments.

A unique signal signature obtained at various configurations pertaining to the volume of dose dispensed by a drug delivery device may be used to obtain a reference signature (calibration curve) of the dose measurement system. FIG. 14 is a graph showing examples of reference signal signatures obtained for a drug delivery device using a dose measurement system that includes a total of seven sensors according to some embodiments. The dose measurement system may be any dose measurement system as described herein. The electromagnetic radiation signature detected by each of the plurality of sensors for a range of dose volumes dispensed is stored and used to create the reference signature. As can be seen from the reference signature when the drug delivery device is almost full, sensor 1 records low amplitude of electromagnetic radiation, while sensor 7 records very high amplitude of electrode and all other sensors detect some intermediate signal signature. In contrast, when the drug delivery is completely empty, sensor 1 records very high amplitude of electromagnetic radiation, while sensor 7 records low amplitude and all other sensors detect some intermediate signal signature.

Sensor 8 detects a uniform sensor signal for a substantial portion of the dose delivered, until the almost all the dose has been delivered or the drug delivery device is almost empty. In some embodiments, the sensor 8 is used as the volume critically low sensor (e.g., to indicate that the drug delivery device is completely empty). In some embodiments, sensor 8 also is used as a usability metric sensor to detect, for example, if a drug delivery device is coupled to the dose measurement system and/or if a component (e.g., an injector) to be included in the drug delivery device is present or not.

Therefore in this manner, the signal value recorded from all sensors for a range of drug volumes remaining yields the signal signature for the entire volume of drug in the drug delivery device. The range of drug volumes used for obtaining the signal signature may include, but is not limited to, completely full, completely empty, and/or a sufficient number of intermediate signatures (e.g., obtained every unit of the total fluid dispensed and/or inclusive of all percentages there between).

In some embodiments, a reference signature may be corrected for background light. For example, a background signature may be detected by detecting the signal signature from the plurality of sensors in a dark state of the plurality of light sources. The signal signature may be compared with the background signature to remove background noise. In some embodiments, the signal signature is associated with the reference signature to determine a drug volume in the drug delivery device, using probabilistic matching algorithms. In some embodiments, the plurality of light sources and the plurality of sensors are configured such that the dose measurement system can detect a volume of drug in the drug delivery device with a resolution of 1 unit of drug, and/or a position of a plunger portion of an actuator disposed in the drug delivery device with a resolution of 100 micrometers, 110 micrometers, 120 micrometers, 130 micrometers, 140 micrometers, 150 micrometers, 160 micrometers, 170 micrometers, 180 micrometers, or 200 micrometers, inclusive of all ranges there between.

Figure 15:
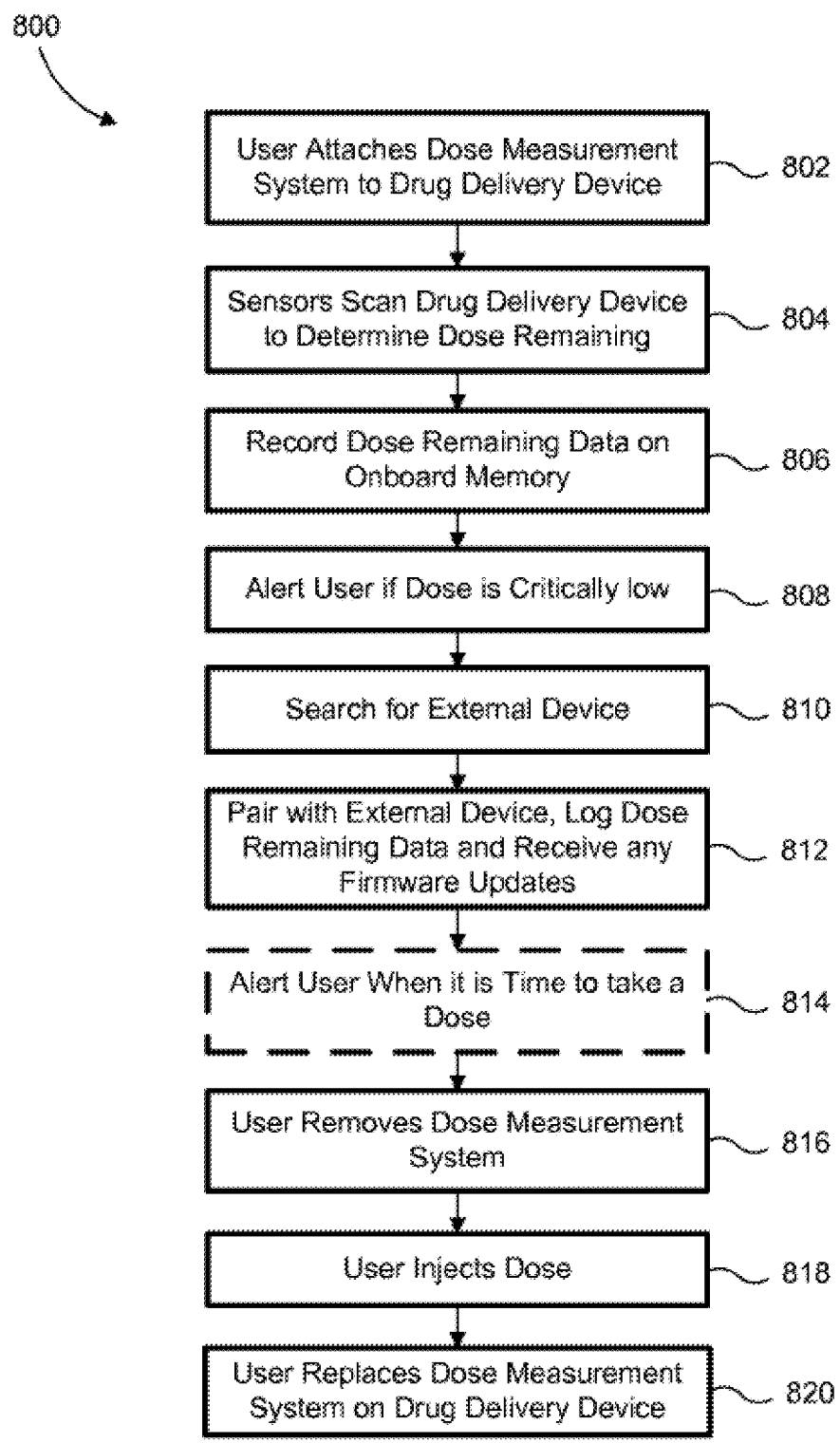
FIG. 15 is a flow diagram of a method of operation of the dose measurement system in accordance with some embodiments.

FIG. 15 a flow diagram illustrating a method 800 for measuring dose remaining in a drug delivery device using any of the dose measurement systems described herein according to some embodiments. In step 802, a user attaches a dose measurement system to a drug delivery device. In step 804, a plurality of sensors disposed in the dose measurement system scan the drug delivery device to determine the dose remaining. For example, a processing unit of the dose measurement system may associate the signal signature detected by the plurality of sensors with a reference signature to determine the dose remaining. In step 806, the sensor data may be recorded on an onboard memory (e.g., an RFID chip and/or a memory that is part of the processing unit of the dose measurement system). In step 808, the dose measurement system may alert the user if the dose remaining is critically low. Audio, visual, and/or tactile indications may be used to alert the user.

In step 810, communications module of the dose measurement system may search for an external device (e.g., a smart phone, a local computer, a remote server, etc.). For example, a Bluetooth® connection may be activated to search for an external device. If the dose measurement system pairs with an external device, in step 812, the system may log dose remaining data on the external device and/or receive any firmware updates.

Optionally, the dose measurement system also may alert a user when it is time to take a dose, as in step 814. After dose data has been recorded and transmitted to an external device, the user can remove the dose measurement system from the drug delivery device in step 816. The user then may administer (e.g., inject) a pre-determined volume of the dose using drug delivery device in step 818. In step 820, the user finally replaces the dose measurement system on drug delivery device. At which point, method 800 may be repeated.

Figure 16:
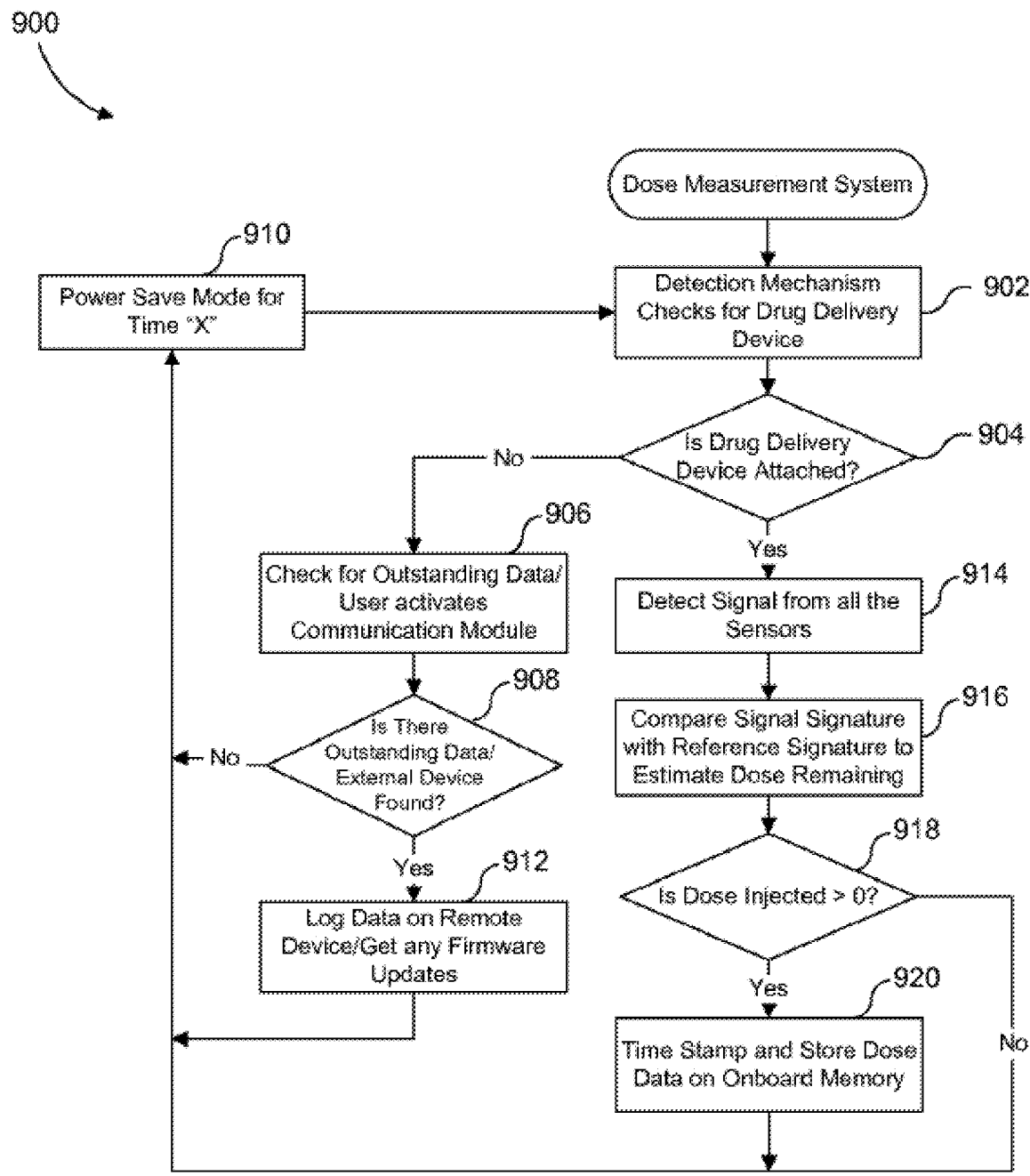
FIG. 16 is a flow diagram of a method of operation of the dose measurement system in accordance with some embodiments.

FIG. 16 is a flow diagram illustrating a method 900 for conserving power when the dose measurement system is not in use according to some embodiments. The method 900 described herein may be used with any of the dose measurement systems described herein. In a first step, a detection mechanism of the dose measurement system checks for a drug delivery device 902. The drug delivery device can either be coupled or uncoupled to the dose measurement system 904. If the drug delivery device is not attached, the dose measurement system automatically checks for outstanding data in the memory to be logged to an external device or the user can activate a communications module of the dose measurement system 906. In some embodiments, the communications module is only activated when the dose measurement system is attached to a drug delivery device. The dose measurement system then determines if there is onboard data to be logged and if an external device was found 908. If there is no onboard data to be logged and no external device was found, the dose measurement system goes into a power save mode for a predefined time "X" 910. For example, a processing unit of the system cans turn off a communications module of the dose measurement system and/or turn off the electronics controlling a plurality of light sources and/or plurality of sensors of the dose measurement system. Time "X" may be, e.g., 1 minute, 10 minutes, 1 hour, or any time there between. Alternatively, if there is data to be logged and an external device was found, the dose measurement system pairs with the external device and logs data on the external device and/or receives any firmware updates from the external device 912. The dose measurement system can then go into the power save mode 910. If instead a drug delivery device was found to be attached to the dose measurement system 904, the dose measurement system scans the drug delivery device and collects signal from all of the plurality of sensors 914. The signal from each of the plurality of sensors may be used to create a signal signature corresponding to the dose remaining in the drug delivery device. A processing unit of the dose measurement system compares the signal signature with a reference signature to estimate dose remaining in the drug delivery device 916. The dose measurement system determines if the dose injected was greater than zero 918. If the dose injected was greater than zero, the dose measurement system time stamps and stores the dose on an onboard memory 920. The dose measurement system then goes into the power save mode for the time "X" 910. If the dose injected was not greater than zero 918, than the dose measurement system directly goes into the power save mode for the time "X" 910.

Figure 17:
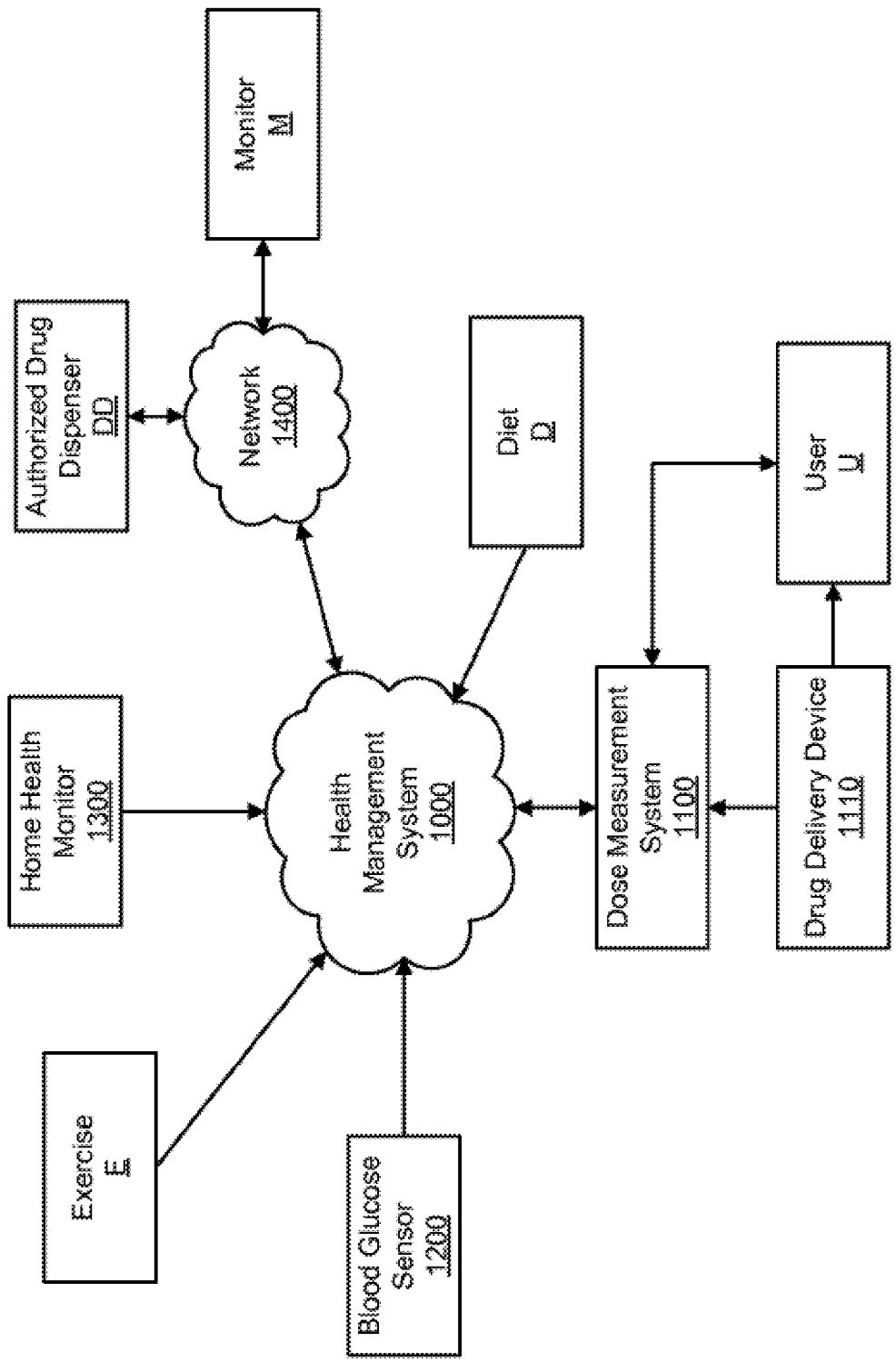
FIG. 17 is a schematic block diagram of a health management system associated with a dose measurement system in accordance with some embodiments.

In some embodiments, any of the dose measurement systems described herein may be associated with a health management system to manage the health of a patient suffering from Type I or II diabetes. FIG. 17 shows a schematic block diagram of a health management system 1000 for managing the health of a diabetic user U according to some embodiments. The health management system may be a mobile application for using, for example, on a smart phone, tablet, or portable computer. In some embodiments, the health management system is a local computer or a remote server.

The health management system may be in two-way communication with a dose measurement system 1100 that is reversibly coupled to a drug delivery device 1110. The drug delivery device 1110 may be an insulin injection pen or syringe for administering insulin to user U. The dose measurement system also may communicate information to a user or receive an input from the user. The health management system 1000 may be configured to receive the user exercise data E and diet data D. The health management system 1000 also may be configured to receive blood glucose data from a blood glucose sensor 1200. The health management system 1000 further may be configured to receive user health data from a home health monitor 1300, e.g., weight, blood pressure, EKG, oxygen saturation, autography measures, pulmonary function, water retention, temperature, etc. The health management system 1000 may be in two-way communication with a network 1400.

The network may be, for example, a remote server or a call center. The network 1400 also may be in two ways communication with a monitor M and an authorized drug dispenser DD. The monitor M may be, for example, a doctor, a caregiver, a pharmacy, and/or a clinical trial manager. The authorized drug dispenser DD may be, for example, a pharmacy or a clinical trial manager.

In some embodiments, the dose measurement system 1100 communicates to the health management system the insulin dose remaining in and/or the insulin dose delivered to user U by the drug delivery device 1110. In some embodiments, the health management system also includes a memory for storing user U insulin dose regimen and/or any other medication schedule. User U medication regimen may be communicated to the health management system 1100 by, for example, the monitor M and/or the authorized drug dispenser DD through the network 1400. In some embodiments, the health management system 1100 also may be used to process user U health data, for example, user U blood glucose levels, exercise data E, diet data D, and/or home health monitored data to determine the status of patient health. In some embodiments, the health management system 1000 also is configured to compare dose delivered to a patient with a patient medication schedule to monitor compliance.

In some embodiments, the health management system can communicate the user health and dose information to the monitor M through the network 1400. The monitor M can analyze user U's health data and determine if any changes to the patient medication plan, for example, insulin and/or any other medication dosage needs to be made. If a change is required, in some embodiments, the monitor M can communicate any changes to user U's medication regimen to the authorized drug dispenser DD. In some embodiments, the monitor M also communicates this information to the health management system 1100 through the network 1400. In some embodiments, the health management system 1100 can update and store user U's medication regimen and also communicate to the dose measurement system 1100, user U's new medication regimen. User U can then access the dose measurement system 1400 to obtain the new measurement plan, for example, new insulin dosage.

In this manner, user U's health may be monitored, user U's diabetes may be managed, and user U's medication schedule may be dynamically personalized to user U. In some embodiments, health management system also communicates user U health and medication history on a periodic basis. The health and medication history may be used, for example, to inform user U of any changes that need to be made to improve user U's overall health. The medication history also may be communicated to the monitor M to analyze user U's progressive health.

Embodiments of the liquid measurement system described herein may include one or more temperature sensors configured to measure a temperature of a liquid and/or a temperature of an environment around the liquid, for example, a temperature of a drug or medication (e.g., insulin) contained within a container (e.g., an injection pen), the container, and/or ambient air around the container. Knowledge of the temperature of the liquid may enable determination of one or more properties of the liquid, including, but not limited to, a level of bioavailability and/or bioefficacy of one or more active components of the liquid, an expiration status of the liquid, and an ease of use of the liquid (e.g., a level of comfort during and following administration of a drug or medication), as well as allow normalization of liquid volume data to compensate for changes or fluctuations in volume of the liquid due to temperature changes or fluctuations. A liquid measurement system that includes one or more temperature sensors as described herein may be any suitable liquid measurement system, for example, an injection pen cap configured to be used with an injection pen (e.g., an insulin injection pen). Examples of such liquid measurement systems are described in the following sources, which are incorporated herein by reference in their entirety:

1. U.S. Pat. No. 8,817,258, entitled "Dose Measurement System and Method," filed Mar. 12, 2013, as U.S. patent application Ser. No. 13/796,889, and issued Aug. 26, 2014;
2. U.S. patent application Ser. No. 14/334,181, entitled "Dose Measurement System and Method," filed Jul. 17, 2014;
3. U.S. Patent Application No. 62/032,017, entitled "Liquid Measurement System with Temperature Sensor," filed Aug. 1, 2014; and
4. U.S. patent application Ser. No. 14/548,679, entitled "Dose Measurement System and Method," filed Nov. 20, 2014.

Embodiments of the liquid measurement system described herein provide several advantages including, but not limited to: (1) enabling real-time measurement of a temperature of a liquid including disposed in a liquid container, for example, a medication and/or its surrounding environment; (2) using temperature information to determine one or more properties of the liquid disposed within the liquid container including, for example, the efficacy, expiration status, ease of administration, or any other physical and/or chemical property of the liquid; (3) providing one or more indications or alerts if a temperature is above or below a predetermined, recommended, and/or allowed range; (4) tracking cumulative exposure of one or more active chemical components of the liquid to heat as it relates to the chemical kinetics of its degradation; and (5) optimizing measurements (e.g., dose volume data or blood glucose data) by compensating for temperature artifacts, for example, normalizing data based on real time temperature measurements to ensure that the data is substantially free of any temperature artifacts.

In some embodiments, a liquid measurement system for measuring a liquid volume in a container includes a plurality of light sources which are disposed and configured to emit electromagnetic radiation toward the container. A plurality of sensors are optically coupleable to the plurality of light sources and are disposed and configured to detect the electromagnetic radiation emitted by at least a portion of the light sources. The apparatus includes a temperature sensor configured to measure a temperature of the liquid disposed in the container. The apparatus also includes a processing unit configured to receive data representing the portion of the detected electromagnetic radiation from each of the plurality of sensors and to convert the received data into a signature representative of the electromagnetic radiation detected by the plurality of sensors. The processing unit of the apparatus described above also is configured to receive temperature information from the temperature sensor and at least one of normalize sensor values, determine efficacy of the liquid, determine expiration status of the liquid, and determine level of administration comfort. In some embodiments, the temperature sensor also is configured to measure the temperature of the environment surrounding the liquid.

Figure 18:
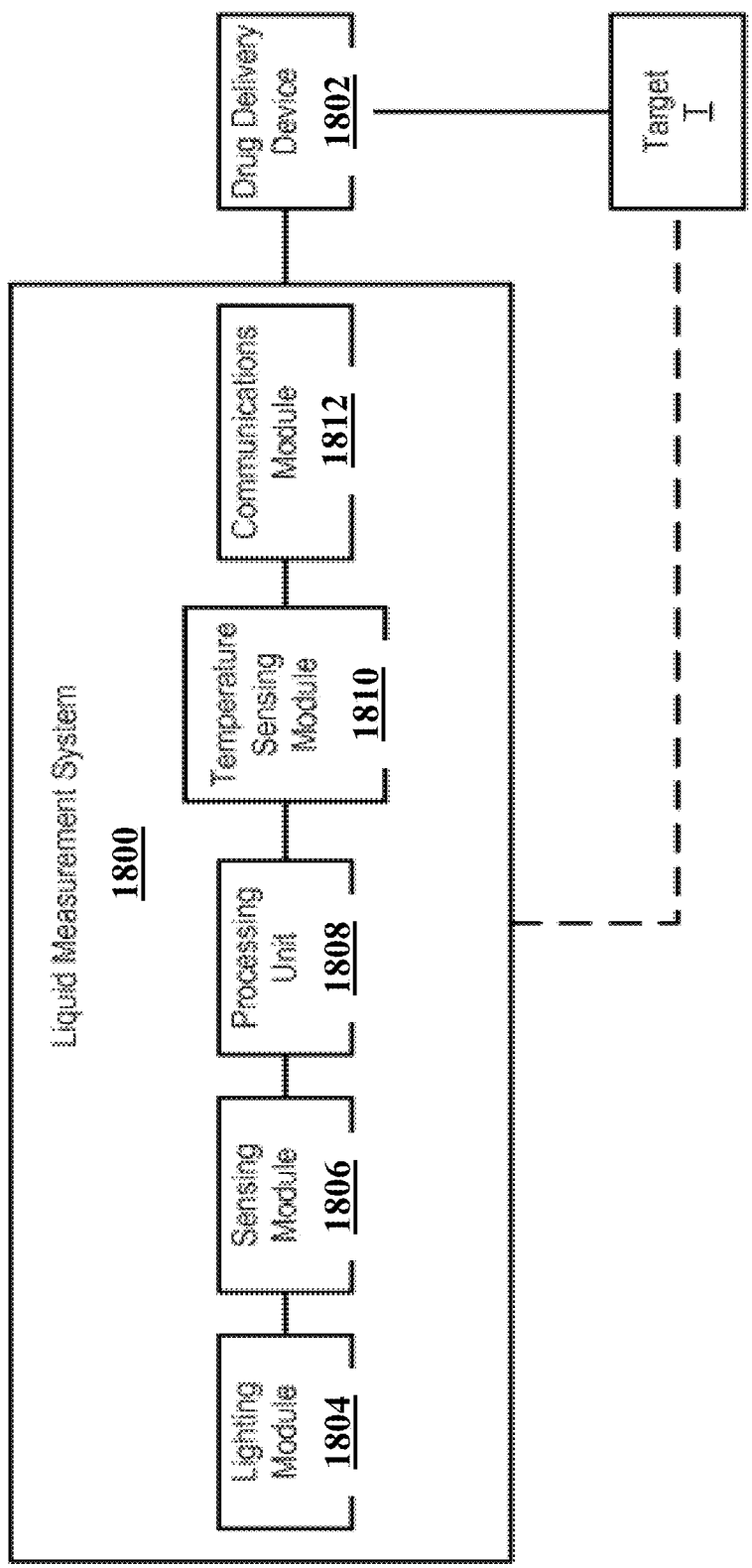
FIG. 18 is a schematic block diagram of a liquid measurement system with a temperature sensing module in accordance with some embodiments.

FIG. 18 is a schematic block diagram of a liquid measurement system 1800 (also referred to herein as a "dose measurement system") for measuring the volume of liquid remaining (also referred to herein as "dose") in a drug delivery device 1802 according to some embodiments. Dose measurement system 1800 includes a lighting module 1804, a sensing module 1806, a processing unit 1808, a temperature sensing module 1810, and a communications module 1812. Dose measurement system 1800 may be configured to be removably coupleable to drug delivery device 1802, which is used to administer a drug dose to a target T, such as, for example, a human patient.

Drug delivery device 1802 may be any drug delivery device that can be used for administering a medication to a subject. For example, drug delivery device 1802 may be an injection pen (e.g., an insulin injection pen), a syringe, a pump (e.g., an insulin delivery pump), an ampoule, and/or a vial. Dose measurement system 1800 may be configured to be coupleable to a wide variety of drug delivery devices having, for example, different shapes, sizes, and drug volumes. In some embodiments, dose measurement system 1800 may be configured to receive a portion of drug delivery device 1802, the portion defining an internal volume including the drug, an injector, and/or a plunger. In some embodiments, dose measurement system 1800 is configured to be removable from drug delivery device 1802 when the user is delivering a dose to target T. In some embodiments, dose measurement system 1800 can remain attached to drug delivery device 1802 when the user is delivering a dose to the target T. In some embodiments, dose measurement system 1800 is configured to be reusable. In some embodiments, dose measurement system 1800 is permanently coupled to drug delivery device 1802, for example, integrated into the body of the drug delivery device. In such embodiments, dose measurement system 1800 may be disposable.

Lighting module 1804 and sensing module 1806 may be configured as described above according to some embodiments. For example, lighting module 1804 may include a plurality of light sources configured to emit electromagnetic radiation towards drug delivery device 1802. Sensing module 1806 may include a plurality of sensors that are optically coupleable to the plurality of light sources of lighting module 1804.

Processing unit 1808 may be configured as described above according to some embodiments. For example, processing unit 1808 may be configured to receive the electromagnetic radiation signal from sensing module 1806 (i.e., from each of the plurality of sensors) and convert the received data into a signal signature representative of the electromagnetic radiation detected by each of the plurality of sensors.

Temperature sensing module 1810 may be configured to measure a temperature of a liquid disposed within drug delivery device 1802 and/or the environment around the liquid, for example, an internal volume of a housing within which the components of dose measurement system 1800 and at least a portion of drug delivery device 1802 are disposed, as described herein. Temperature sensing module 1810 may include one or more suitable temperature sensors, including, but not limited to, thermocouples, resistive temperature devices (RTDs), thermistors, bimetallic temperature sensors, and/or silicon diodes.

One or more temperature sensors may be positioned, configured, attached to, and/or disposed within dose measurement system 1800 for substantially accurate temperature readings of the liquid and/or the environment surrounding the liquid. For example, a temperature sensor may be positioned a sufficient distance from one or more components of dose measurement system 1800 that could impact temperature readings, such as higher temperature electronics (e.g., included in processing unit 1808), a power source (e.g., a rechargeable battery), and/or any other heat generating electronics. Furthermore, a temperature sensor may be positioned in sufficient proximity to the liquid disposed in drug delivery device 1802 to allow heat to diffuse equally to the temperature sensor and the liquid such that the temperature sensor and the liquid are at substantially the same temperature.

In some embodiments, temperature sensing module 1810 includes a single temperature sensor. In other embodiments, temperature sensing module 1810 includes a plurality of temperature sensors positioned in any suitable configuration, including, but not limited to, a straight row, a rectangular array, a square array, a circular array, and/or any other suitable configuration. In some embodiments, temperature sensing module 1810 includes a first temperature sensor or a first set of temperature sensors positioned and/or configured to measure a temperature substantially of the liquid, and a second temperature sensor or a second set of temperature sensors positioned and/or configured to measure a temperature substantially of the environment surrounding the liquid.

In some embodiments, temperature sensing module 1810 includes a printed circuit board (PCB) and/or other electronics configured to process the temperature measurement and/or communicate the temperature information to, for example, processing unit 1808 and/or communications module 1812 for further processing and/or to communicate a temperature measurement to a user.

In some embodiments, temperature sensing module 1810, processing unit 1808, and/or an external computing device process temperature data. Temperature data may be used to determine one or more properties of a liquid and/or an environment surrounding the liquid in dose measurement system 1800, including one or more properties of embodiments of the systems, apparatus, and methods described herein.

In particular, temperature may affect signal quality (e.g., measurements of a quantity of a liquid using sensing module 1806) according to some embodiments. Temperature data may be used to normalize data received from sensing module 1806 such that the sensor data is substantially free of any artifacts or contribution caused by extreme temperatures and/or temperature changes or fluctuations. Due to component changes over temperature, optical measurement sensor readings drift over temperatures. In some embodiments, this sensor drift over temperature is substantially linear. In some embodiments, the lighting module 1804 and sensing module 1806 are optimized to maintain substantially linear sensor drift over temperature.

In some embodiments, temperature sensing module 1810, processing unit 1808, and/or an external computing device may be used to perform a temperature calibration. For example, an external temperature measurement system that includes an independent temperature sensor may be used to obtain a calibration temperature. A positive offset or a negative offset may be calculated based on a difference between an external calibration temperature and an internal temperature measured by a temperature sensor in temperature sensing module 1810. The positive offset or the negative offset may be added to future internal temperature readings.

Extreme temperatures and/or temperature changes or fluctuations may also affect one or more properties of a liquid or a component of the liquid being measured as well as one or more properties of an additional component of or associated with some embodiments, such as accuracy of a glucose meter test strip or glucometer. For example, the bioavailability, bioefficacy, and shelf life of a medication are highly dependent on the temperatures to which the medication is exposed and/or at which the medication is stored. Drug delivery devices, particularly injection pens, that contain such medications or additional components are often carried by a patient, for example, in the patient's pocket, backpack, purse, luggage, etc. Thus, medications may be exposed to widely varying ambient temperatures with impacts on at least the administration, cost, and safety associated with said medications.

For example, the effectiveness of insulin may be degraded by high temperatures. If a patient is dosed with ineffective insulin, he or she may develop hyperglycemia. Manufacturers instruct users to discard insulin that has been exposed to such high temperatures, which happens frequently by accident. Even though the ambient temperature may be below a maximum threshold temperature to preserve quality (e.g., higher than about 37° C. or 98.6° F.), the temperature of the insulin itself may exceed ambient temperature when its container is exposed to sunlight or radiant heat. The maximum threshold temperature to preserve quality may change (e.g., be lower) once the container has been opened (e.g., higher than about 30° C. or 86° F.). Similarly, insulin quality may be affected by low temperatures. For example, manufacturers instruct users not to store insulin in a refrigerator once the container has been opened.

According to some embodiments, guidelines like a maximum threshold temperature, a minimum threshold temperature, a range of temperature, a rate of temperature change, a frequency of temperature fluctuations, and/or a time period of temperature exposure is recommended, allowed, and/or determined to be acceptable based on at least one of the particular liquid measurement system (e.g., dose measurement system 1800), the particular liquid container (e.g., drug delivery device 1802), and the particular liquid (e.g., insulin). Temperature sensing module 1810, processing unit 1808, and/or an external computing device may be configured to compare one or more temperature readings from a liquid and/or its environment to these metrics to determine whether a user should be notified, for example, via an indication, alert, and/or alarm (e.g., via communications module 1812), that, for example, a predetermined number of temperature readings: (1) have exceeded a recommended, allowed, and/or determined maximum threshold temperature value; (2) have dropped below a recommended, allowed, and/or determined minimum threshold temperature value; (3) are outside a recommended, allowed, and/or determined range of temperature values; (4) indicate a rate of temperature change that exceeds a recommended, allowed, and/or determined rate; (5) indicate a frequency of temperature fluctuations that exceeds a recommended, allowed, and/or determined frequency; and/or (6) indicate a time period of temperature exposure longer than is recommended, allowed, and/or determined to be acceptable.

Communications module 1812 may be configured as described above according to some embodiments. For example, communications module 1812 may be configured to allow two-way communication with a user and/or an external device. In some embodiments, communications module 1812 includes a display configured to communicate a status of dose measurement system 1800 to the user, including, but not limited to, dose remaining, history of use, remaining battery life, wireless connectivity status, temperature of a drug, temperature of dose measurement system 1800, temperature of drug delivery device 1802, efficacy of the drug, expiration status of the drug, quality of the drug, and/or a reminder to administer the drug.

Dose measurement system 1800 may be disposed in a housing that can be configured to be removably coupleable to drug delivery device 1802. For example, lighting module 1804, sensing module 1806, processing unit 1808, temperature sensing module 1810, and communications module 1812 may be incorporated into a housing. Alternatively, individual components of dose measurement system 1800 (e.g., lighting module 1804 and sensing module 1806) may be incorporated into a first housing and other components (e.g., processing unit 1808, temperature sensing module 1810, and communications module 170) may be separate or incorporated into a second housing. In some embodiments, a housing is configured (e.g., shaped and sized) to be removably coupled to at least a portion of drug delivery device 1802. For example, the housing may have a recess and/or may define a bore into which at least a portion of drug delivery device 1802 can be received.

Having described above various general principles, several exemplary embodiments of these concepts are now described. These embodiments are only examples, and many other configurations of a liquid measurement system, particularly a dose measurement system for measuring dose delivered to a patient and/or remaining in a drug delivery device, that account for temperature effects are envisioned.

Figure 19:
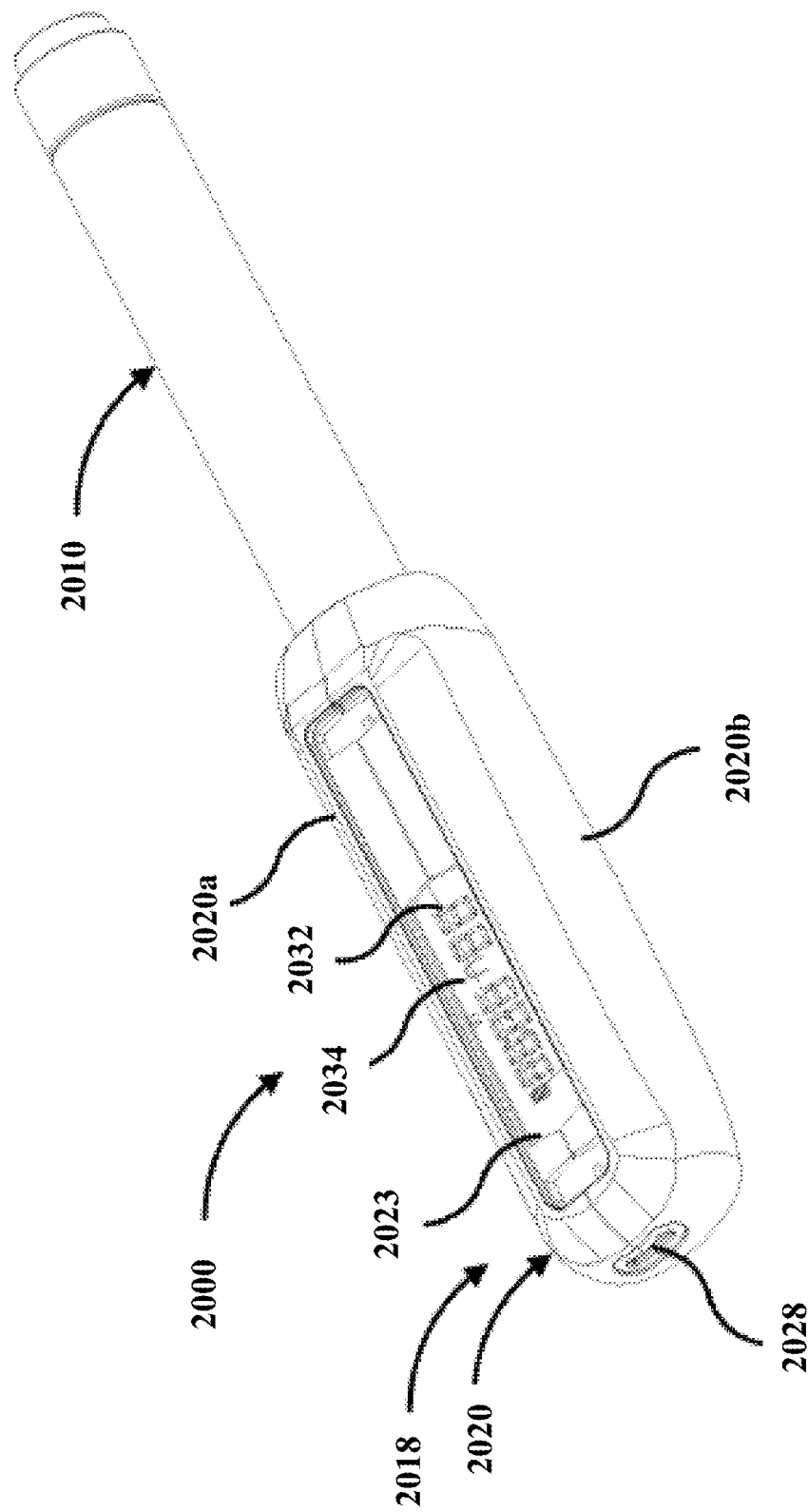
FIG. 19 is a perspective view of a liquid measurement system with a temperature sensing module in accordance with some embodiments.
Figure 20:
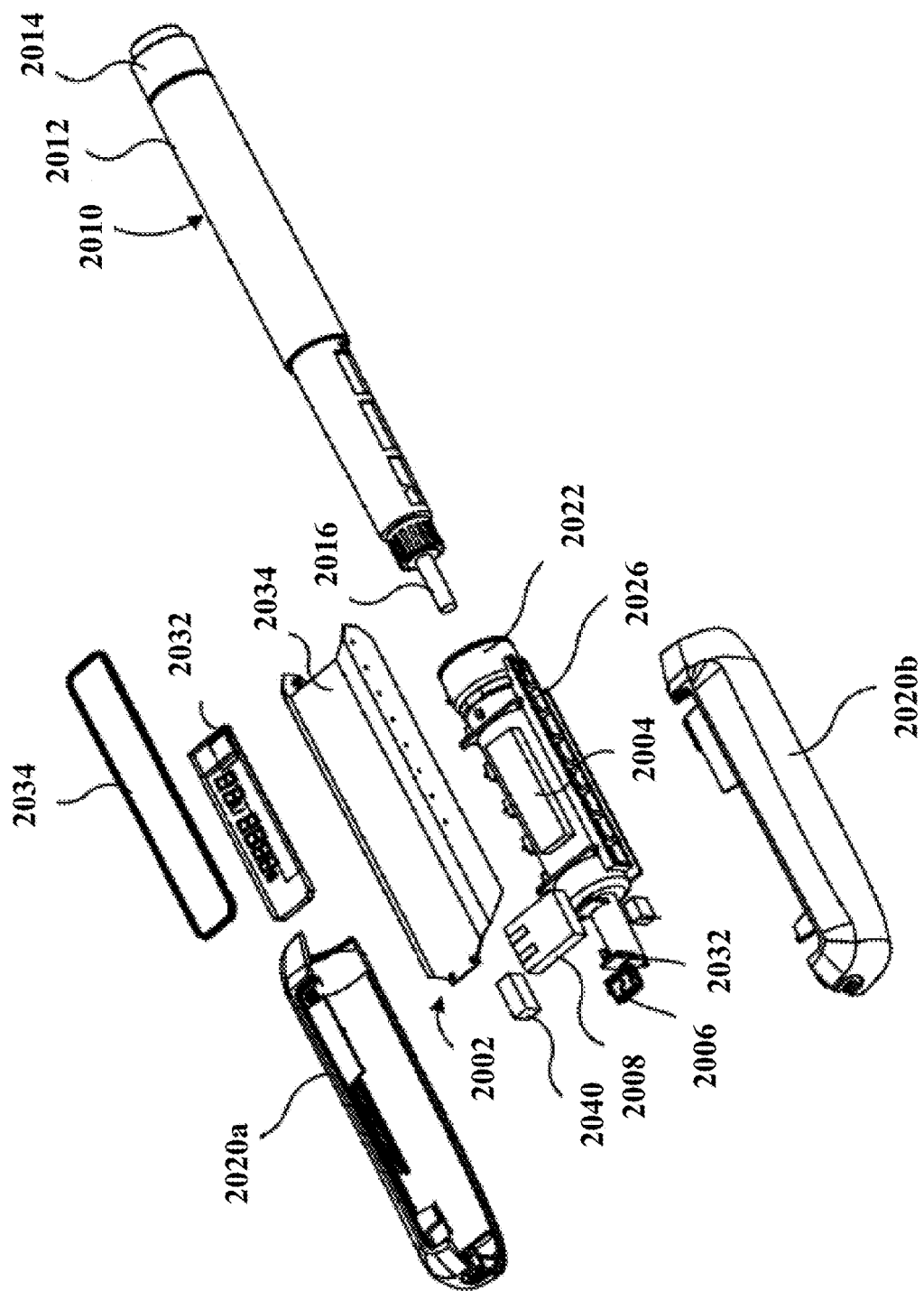
FIG. 20 is an exploded perspective view of the liquid measurement system of FIG. 19 in accordance with some embodiments.
Figure 21:
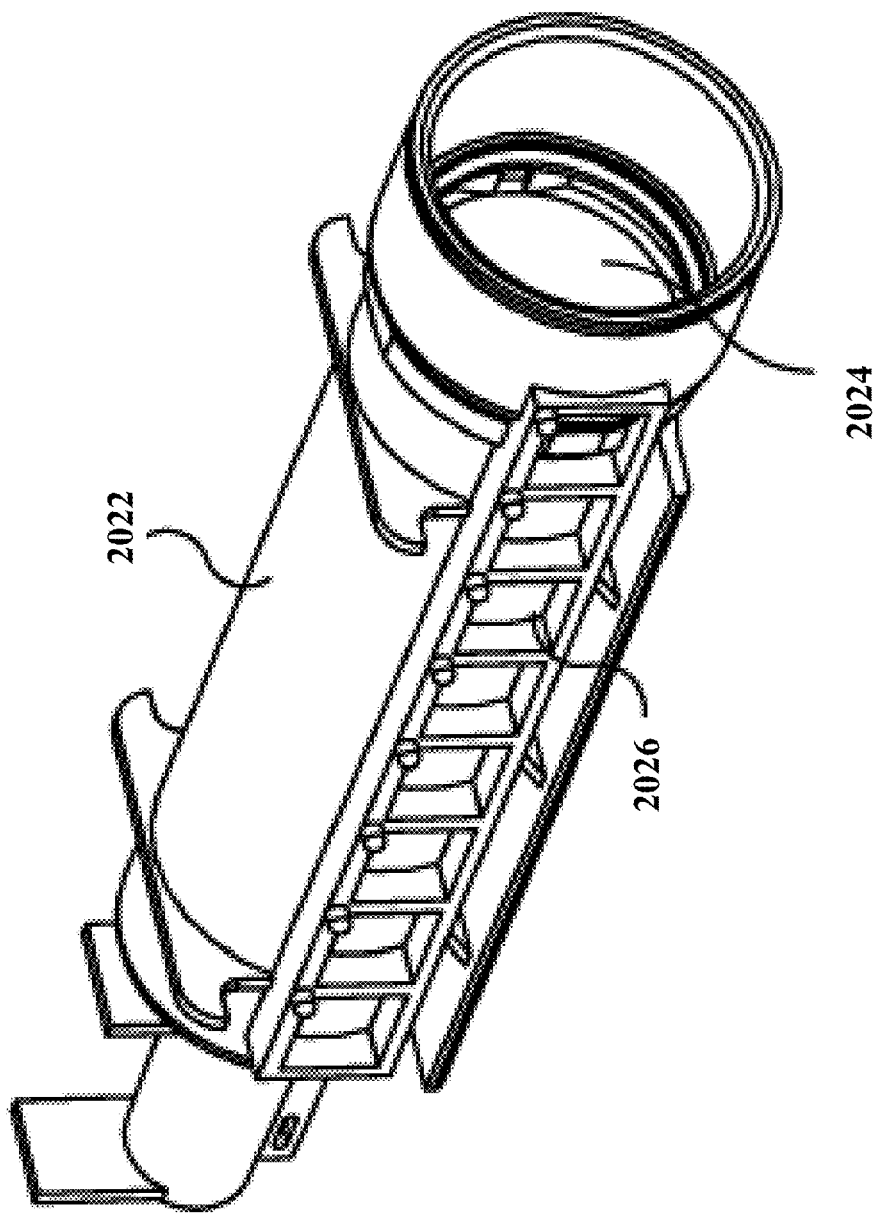
FIG. 21 shows a back perspective view of a bottom housing included in the liquid measurement system of FIG. 20 in accordance with some embodiments.
Figure 22:
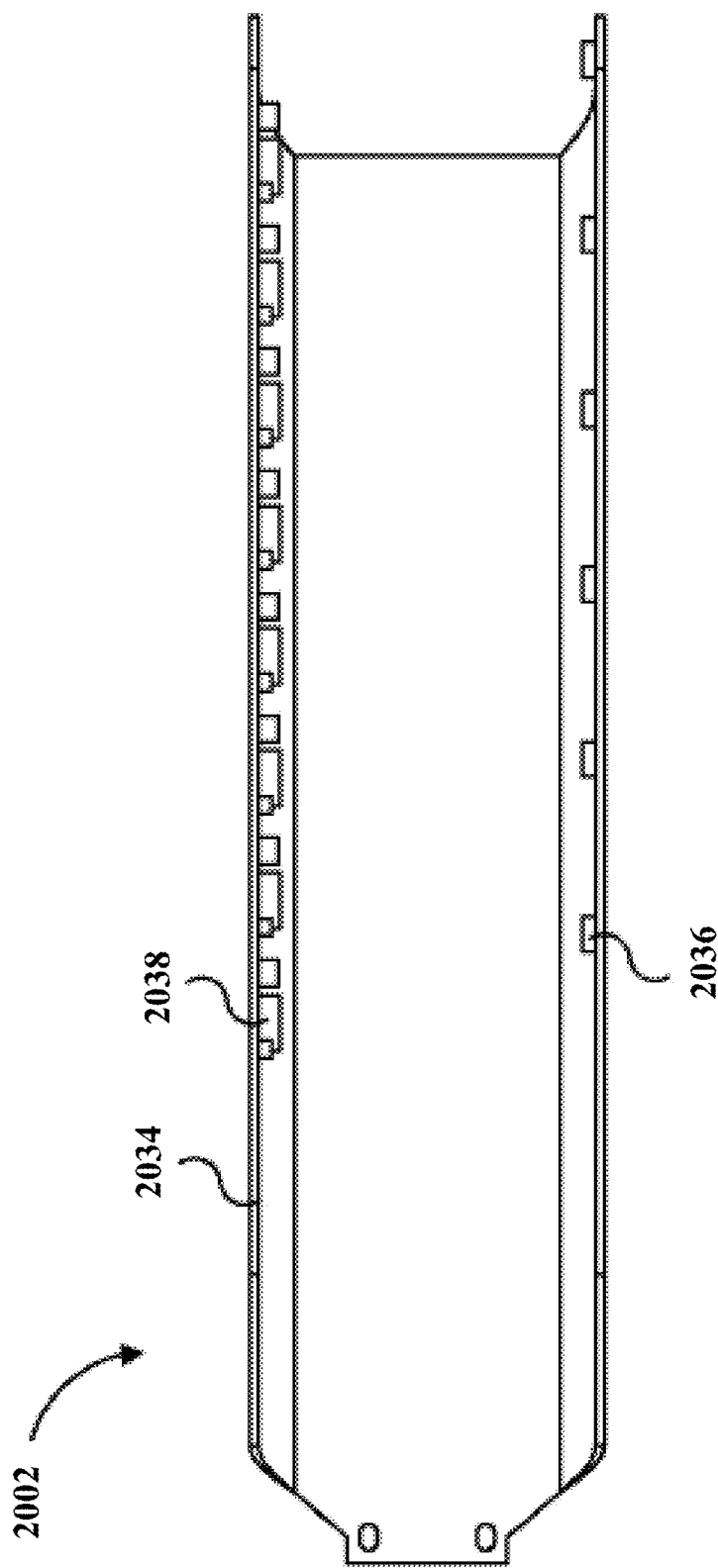
FIG. 22 is a bottom view of a PCB included in a sensing assembly of the liquid measurement system of FIG. 21 in accordance with some embodiments.

Referring now to FIGS. 19-22, a liquid measurement system 2000 (also referred to herein as "dose measurement system 2000") may include a sensing assembly 2002, a temperature sensing module 2004, a communications module 2006, and a power source 2008 according to some embodiments. FIG. 19 is a perspective view of liquid measurement system 2000. FIG. 20 is an exploded perspective view, FIG. 21 is a back perspective view of a bottom housing, and FIG. 22 is a bottom view of a PCB included in sensing assembly 2002 of dose measurement system 2000.

Dose measurement system 2000 may be configured to be removably coupleable to a drug delivery device 2010 (also referred to herein as an "injection pen 2010"). Drug delivery device 2010 may be configured to deliver a predefined quantity (i.e., dose) of a liquid drug (e.g., insulin) to a patient. Examples of drug delivery device 2010 include insulin injection pens that may be used by a patient to administer insulin. According to some embodiments, as shown in FIG. 20, drug delivery device 2010 includes a housing 2012, an actuator 2014, and an injector 2016. Housing 2012 may be relatively opaque, such that it only allows select wavelengths of electromagnetic radiation (e.g., infrared or microwave radiation) to be transmitted there through. Housing 2012 may define an internal volume (e.g., a reservoir) for storing a drug. Actuator 2014 may include a plunger portion in fluid communication with the drug and configured to communicate a predefined quantity of the drug to the patient. Actuator 2014 may be configurable, for example, by the user, to dispense variable quantities of the drug. Injector 2016, (e.g., a needle) may be configured to penetrate a user's tissue for intramuscular, subcutaneous, and/or intravenous delivery of the drug. Housing 2012 may be configured such that temperature sensing module 2004 can measure a temperature of the drug directly or indirectly via housing 2012, actuator 2014, and/or injector 2016.

In some embodiments, and as shown in FIG. 19, dose measurement system 2000 includes a housing 2018 that includes a top housing portion 2020 (also referred to herein as "top housing 2020") and a bottom housing portion 2022 (also referred to herein as "bottom housing 2022"). Top housing portion 2020 includes a first portion 2020a and a second portion 2020b that may be coupled together to the form the top portion 2020. The first portion 2020a and the second portion 2020b may be removably or fixedly coupled together by, for example, gluing, hot welding, a snap-fit mechanism, one or more screws, and/or by any other suitable means. Furthermore, the top housing 2020 and bottom housing 2022 may be removably or fixedly coupled together by, for example, gluing, hot welding, mechanical coupling (e.g., one or more snap-fit mechanisms or screws), and/or by any other suitable coupling means.

Housing 2018 may be made from a rigid, lightweight, and/or opaque material, including, but not limited to, polytetrafluoroethylene, high density polyethylene, polycarbonate, other plastics, acrylic, sheet metal, any other suitable material, or a combination thereof. Housing 2018 also may be configured to shield the internal electronic components of dose measurement system 2000 from environmental electromagnetic noise. For example, housing 2018 may include an insulation structure such as, for example, aluminum lining or any other metal sheet or foil that can serve as an electromagnetic shield.

As shown in FIG. 19, first housing portion 2022a and second housing portion 2022b may define an internal volume for substantially housing sensing assembly 2002, temperature sensing module 2004, communications module 2006 and power source 2008. As shown in FIG. 21, bottom housing portion 2022 may define a bore 2024. Bore 2024 may be shaped and sized to receive at least a portion of drug delivery device 2010. For example, bore 2024 may be shaped and sized to receive only the drug-containing portion of housing 2012 and injector 2016. Bore 2024 may be configured to receive drug delivery device 2010 in a particular orientation (e.g., a radial orientation). In some embodiments, bore 2024 is in close tolerance with a diameter of drug delivery device 2010, for example, to form a friction fit with drug delivery device 2010. In some embodiments, bore 2024 includes one or more notches, grooves, detents, snap-fit mechanisms, threads, and/or other coupling mechanisms for removably coupling drug delivery device 2010 to the bottom housing 2022. In some embodiments, bottom housing portion 2022 includes one or more alignment features for removably coupling drug delivery device 2010 to be coupleable with dose measurement system 2000 in a predetermined radial orientation.

In some embodiments, bottom housing 2022 defines one or more apertures 2026 for receiving at least a portion of a plurality of light sources which may be included in a lighting module of the sensing assembly 2002, and/or sensors including in a sensing module of the sensing assembly 2002. The one or more apertures 2026 may be configured to provide mechanical support for the light sources and/or sensors, and may serve as an alignment mechanism for the lighting and/or sensing modules.

As shown in FIG. 19, top housing 2020 may define an opening 2028 for receiving at least a portion of communications module 2006, such as, for example, a communication interface to provide wired communication with an external device, and/or an interface for charging power source 2008. As shown in FIGS. 19 and 20, top housing 2020 may define a slot 2030 for viewing a display 2032 included in communications module 2006, as described herein. A transparent layer 2034, such as, for example, a glass, acrylic (e.g., Plexiglas®), or plastic sheet, may be disposed below the slot 2030 to protect the display 2032 and to provide a window for viewing the display 2032.

In some embodiments, housing 2018 also includes a detection mechanism (not shown) to detect if drug delivery device 2010 has been coupled to dose measurement system 2000. The detection mechanism may include, for example, a push switch, a motion sensor, a position sensor, an optical sensor, a piezoelectric sensor, an impedance sensor, and/or any other suitable sensor. Housing 2018 may be relatively smooth and free of sharp edges. In some embodiments, housing 2018 is shaped to resemble a pen cap that has a form factor that occupies minimal space, for example, can fit in the pocket of a user. In some embodiments, housing 2018 also includes features, for example, clips for attaching to a user's shirt pocket, and/or other ornamental features. In some embodiment, dose measurement system 2000 also serves as a replacement cap for drug delivery device 2010.

Sensing assembly 2002 may include a lighting module, a sensing module, and a processing unit which may be configured to determine a dose remaining in drug delivery device 2010. Sensing assembly may include a printed circuit board (PCB) 2034 on which the lighting module, the sensing module, and the processing unit may be mounted, as shown in FIG. 22. The lighting module and the sensing module may be substantially similar to lighting module 1804 and sensing module 1806 described with respect to dose measurement system 1800, as described above. Furthermore, the processing unit may be substantially similar to processing unit 1808, as described above.

In some embodiments, the lighting module includes a plurality of light sources 2036 disposed on the PCB 2034 which may be configured to produce an electromagnetic radiation of a wavelength that is capable of penetrating through housing 2012 of drug delivery device 2010, the drug contained therein, and/or a portion of housing 2018. For example, infrared radiation or microwave radiation can penetrate many of the plastic materials that are commonly used in manufacturing drug delivery devices (e.g., injection pens). In some embodiments, an electromagnetic radiation has a frequency that can penetrate through the internal components of drug delivery device 2010, for example, the plunger portion of actuator 2014. In some embodiments, the light sources 244 are configured to produce a wide beam of electromagnetic radiation, for example, wide angle LEDs or a single LED connected to a light pipe splitting emitted electromagnetic radiation into a plurality of wide angle beams). Said another way, the electromagnetic radiation cone of a single light source 244 can have a wide angle and the electromagnetic radiation cones of adjacent light sources 244 can overlap. In some embodiments, the plurality of light sources 2036 are configured to emit pulses of electromagnetic radiation (e.g., a series of less than 100 microsecond pulses).

The sensing module may include a plurality of sensors 2038 which may be mounted, or otherwise disposed on, the PCB 2034 included in the sensing module 230, as shown in FIG. 5. The PCB 252 may be any standard PCB made by any commonly known process. The plurality of sensors 2038 may be any optical sensors (e.g., photodiodes) optically coupleable with the plurality of light sources 2036 and configured to detect at least a portion of the electromagnetic radiation emitted by the plurality of light sources 2036. The electromagnetic radiation may be transmitted radiation, refracted radiation (refracted by, e.g., air, drug, and/or body of drug delivery device 2010), reflected radiation (reflected from, e.g., a wall of housing 2018 or internally reflected from a wall of drug delivery device 2010), and/or multi-directional refraction/reflection (caused by, e.g., a lensing effect of a curved surface of housing 2012). The transmitted, refracted, and/or reflected electromagnetic signal received by the plurality of sensors 2038 may be used to create a signal signature (e.g., by the processing unit). The signal signature may be associated with a reference signature to determine the dose remaining in drug delivery device 2010. In some embodiments, the signal response of the sensors 2038 may be used to measure usability metrics such as determining, for example, the presence of injector 2016 of drug delivery device 2010 and/or whether drug delivery device 2010 is coupled or uncoupled with dose measurement system 2000. In some embodiments, the signal response of the sensors 2038 may be processed further (e.g., calibrated) based on temperature data.

Temperature sensing module 2004 may include one or more temperature sensors configured to measure the temperature of the liquid disposed within drug delivery device 2010 and/or the environment around the liquid, for example, the internal volume of bore 2024 of bottom housing 2022 within which at least a portion of drug delivery device 2010 may be disposed. The one or more temperature sensors may include one or more thermocouples, RTDs, thermistors, bimetallic temperature sensors, silicon diodes, and/or any other suitable temperature sensors. One or more temperature sensors may be positioned and/or disposed in the internal volume defined by top housing 2020a to allow substantially accurate temperature readings of the liquid volume and/or the environment surrounding the liquid. For example, the one or more temperature sensors may be disposed along an outer surface of a sidewall of bottom housing 2020b.

Furthermore, one or more temperature sensors may be positioned a sufficient distance away from any components of dose measurement system 2000 that can impact temperature readings such as, for example, higher temperature electronic component 2040 (e.g., a capacitor or resistor) or power source 2008 as shown in FIG. 20. Furthermore, one or more temperature sensors may be disposed in sufficient proximity to the liquid volume disposed in drug delivery device 2010 so that the diffusion of heat to the one or more temperature sensors and the liquid is substantially equal and the one or more sensors accurately reflect the temperature of the liquid. In some embodiments, temperature sensing module 2004 includes a first temperature sensor or a first set of temperature sensors configured to solely measure the temperature of the liquid, and a second temperature sensor or a second set of temperature sensors configured to solely measure the temperature of the environment surrounding the liquid. In some embodiments, temperature sensing module 2004 consists of a single temperature sensor. In other embodiments, temperature sensing module 2004 includes a plurality of temperature sensors disposed in, for example, a straight row, a rectangular array, a square array, a circular array, or any other suitable configuration. In some embodiments, temperature sensing module 2004 includes a printed circuit board (PCB) and/or other electronics configured to process data and/or communicate temperature data to, for example, communications module 2006.

In some embodiments, temperature sensing module 2004 includes a processing unit. In some embodiments, temperature sensing module 2004 is configured to communicate temperature data to the processing unit included in the sensing assembly 2002. At least one processing unit is configured to use the temperature data to determine a quality of the liquid (e.g., a bioavailability, bioefficacy, and/or expiration status of one or more components) and/or a quality of administration (e.g., a level of ease and/or comfort). For example, information on thermal stability and efficacy of a liquid drug disposed in drug delivery device 2010 may be stored in memory coupled to a processing unit. The processing unit may compare a real-time temperature of the liquid drug and/or the environment surrounding the drug provided by temperature sensing module 2004 with the thermal stability information for the particular drug to determine a physical and/or chemical status/quality of the drug. In some embodiments, thermal stability information for a multitude of drugs (e.g., insulin, epinephrine, etc.) or just a particular drug may be stored in an external or internal memory device communicatively coupled to the processor, thereby allowing dose measurement system 2000 to be compatible with different drug delivery devices that may contain different drugs, a particular drug delivery device that may contain different drugs, different drug delivery devices that contain a substantially similar drug, or a particular drug delivery device that contains a substantially similar drug.

In some embodiments, temperature data is used to normalize or correct data received from the sensing module so that the sensor data (i.e., the signal signature) is substantially free of any artifacts or contributions caused by extreme temperatures, temperature changes, and/or temperature fluctuations.

Figure 23:
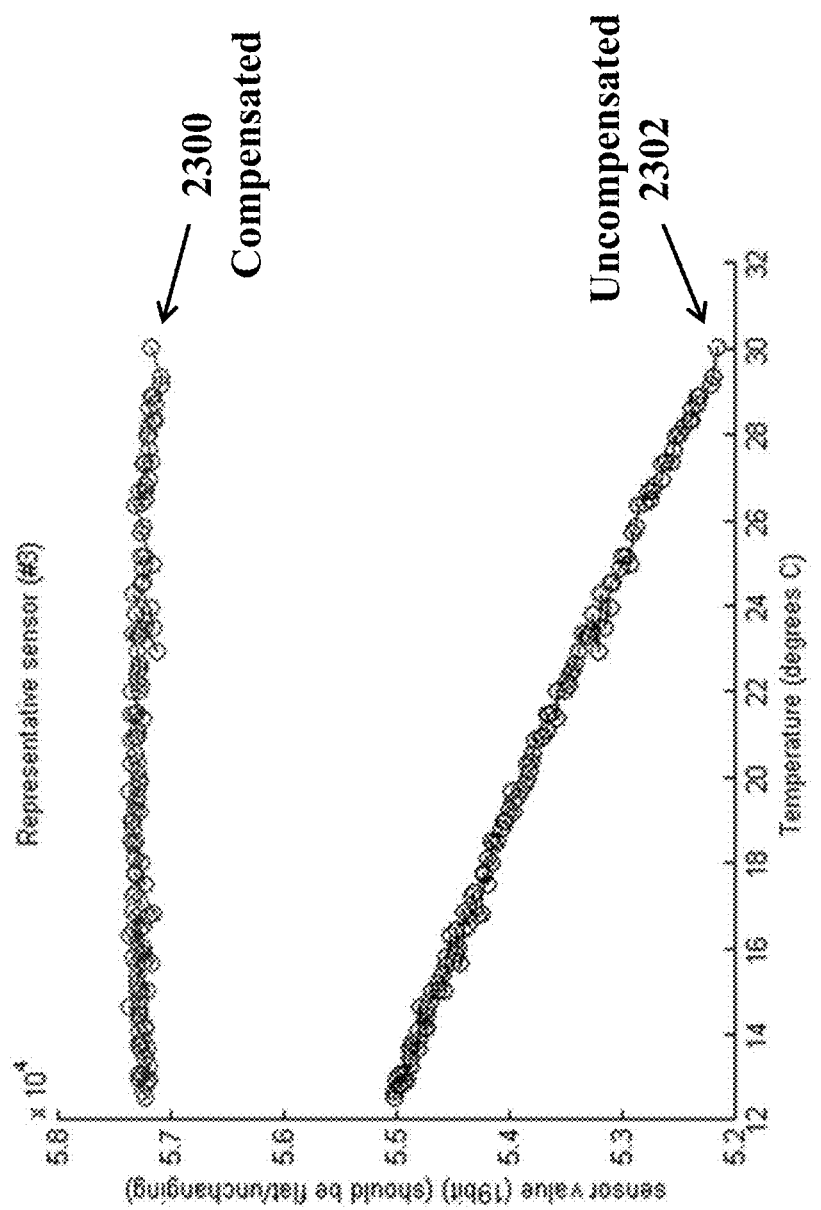
FIG. 23 is a graph showing compensated and uncompensated measurements of a representative sensor of a liquid measurement system as a function of temperature in accordance with some embodiments.

FIG. 23 is a graph showing compensated measurements 2300 and uncompensated measurements 2302 of a representative sensor of a liquid measurement system as a function of temperature in accordance with some embodiments. The uncompensated sensor measurements 2302 may diverge substantially from actual temperature as the actual temperature changes and/or fluctuates. In some embodiments, it may be preferable to adjust temperature measurements as the actual temperature changes and/or fluctuates, thereby generating compensated measurements 2300 in order to more accurately monitor the real temperature of the remaining liquid.

In some embodiments, compensation for temperature change is achieved by applying the following correction factor:

$$A \times \Delta T \times S_{raw} \quad (1)$$

where A is a scaling constant that may vary according to the individual sensor design, $S_{raw}$ is the unprocessed sensor reading, and $\Delta T$ is the difference between the measured temperature and a baseline temperature, which may be any temperature (e.g., 0° C.) as long as it remains constant:

$$\Delta T = T_{meas} - T_{base} \quad (2)$$

Thus, a compensated sensor value may be determined according to:

$$S_{comp} = S_{raw} + A \times \Delta T \times S_{raw} \quad (3)$$

In some embodiments, the scaling constant accounts for saturation edge cases. If a particular sensor is already saturated, the sensor may not be allowed to be under saturated due to temperature compensation.

Temperature data also may be used to normalize the calibration signature, for example, if the calibration was performed at a first temperature, and the signal signature is measured at a second temperature different from the first temperature. In some embodiments, sensor data is normalized with respect to the thermal expansion coefficient of the drug using the temperature data. In this manner any errors due to volumetric expansion or contraction of the liquid drug or other temperature-related interference with the sensor may be corrected.

In some embodiments, a processing unit is configured to perform temperature calibrations. For example, in such embodiments, the processing unit may be configured to receive a calibration temperature measured by an external temperature measurement system that includes an independent temperature sensor. A positive offset or a negative offset may be generated based on the difference between the external calibration temperature and an internal temperature measured by the temperature sensor included in temperature sensing module 2004. For any future temperature sensing, the processing unit can then calculate the final temperature reading by adding the positive offset or the negative offset to the internal temperature.

Figure 24:
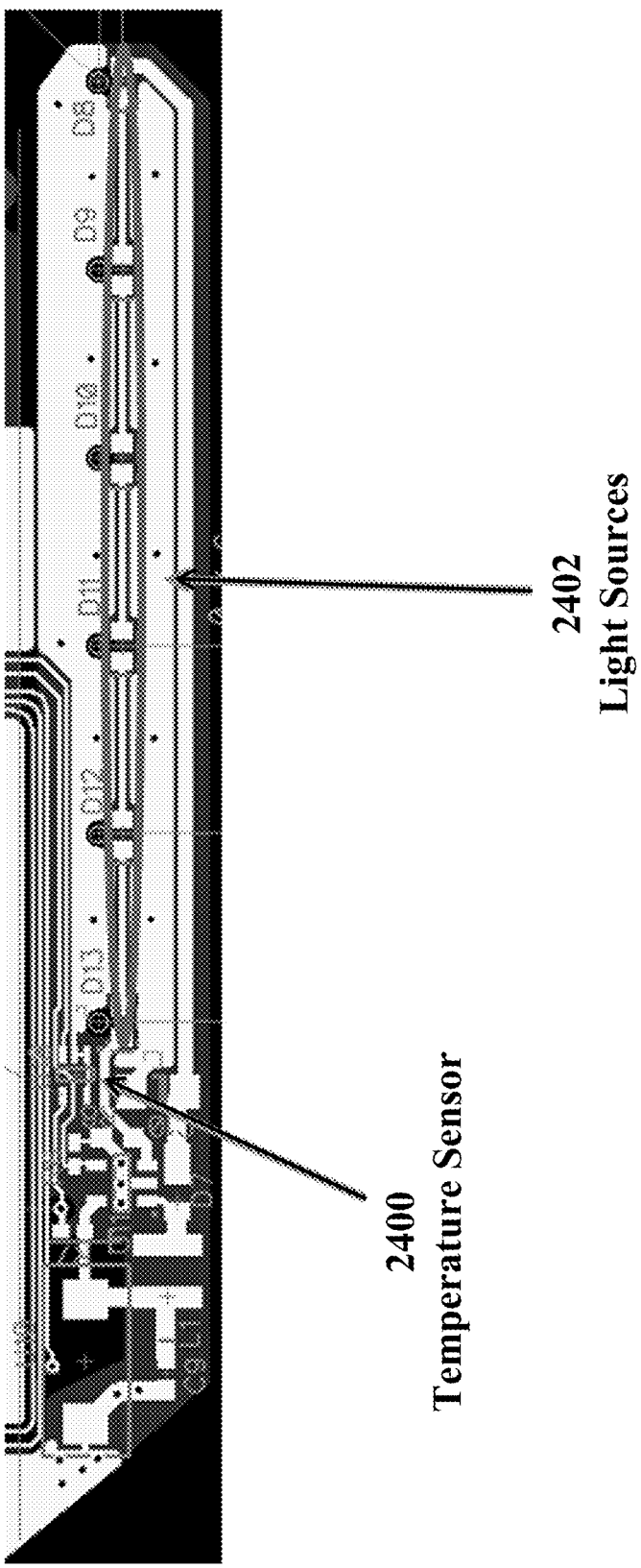
FIG. 24 is a diagram of part of a liquid measurement system including a temperature sensor in accordance with some embodiments.
Figure 25:
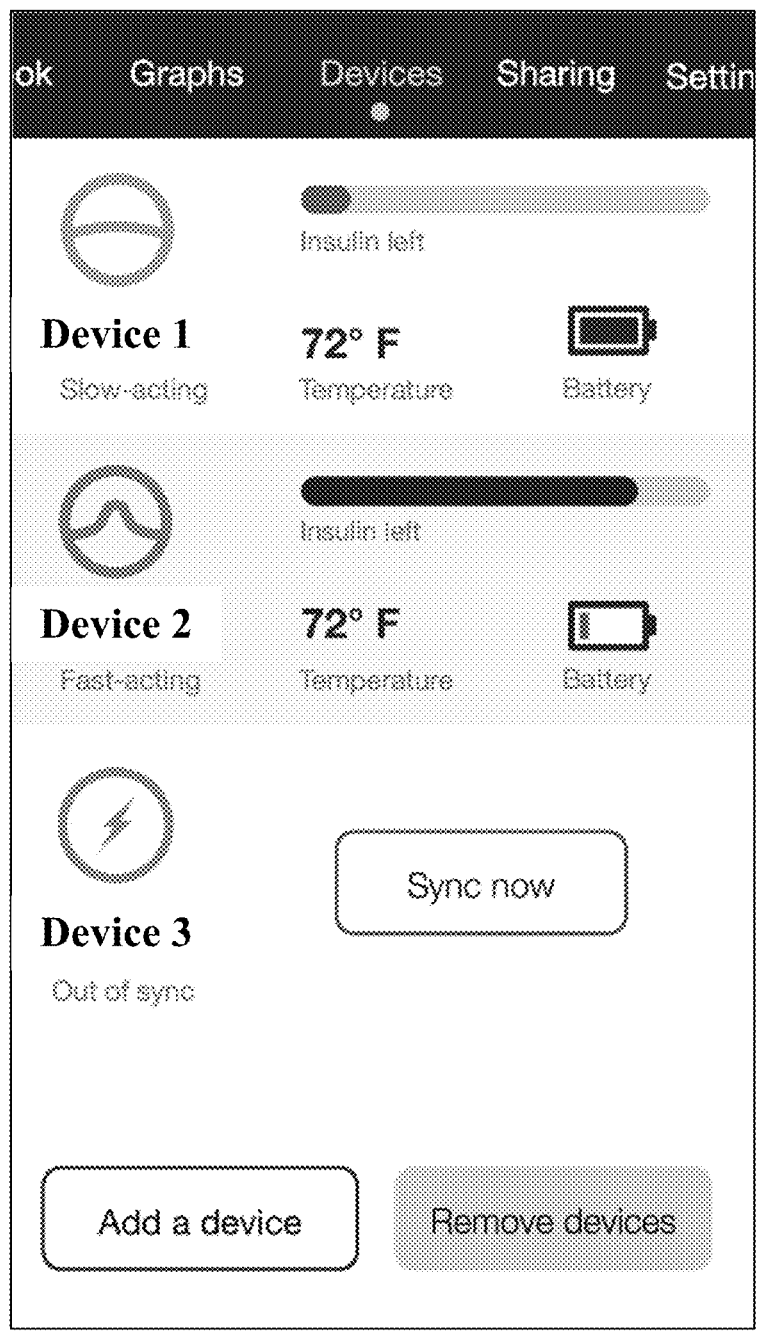
FIG. 25 is a screenshot of a user interface display for monitoring one or more liquid measurement systems in accordance with some embodiments.

Placement of a temperature sensor is important to accurate temperature compensation and/or calibration. In some embodiments, a temperature sensor is placed in close proximity to the components that most vary over temperature. In some embodiments, the component that varies most over temperature is an emitters or light source. In FIG. 24 a diagram of part of a dose measurement system shows a temperature sensor 2400 placed in close proximity to the light sources 2402 (e.g., a plurality of LEDs or a single LED connected to a light pipe splitting emitted electromagnetic radiation into the plurality of light sources) in accordance with some embodiments.

Temperature is also a key factor affecting blood glucose measurement. The temperature(s) at which test strips are stored and at which a glucose meter or glucometer is operated are both important. In particular, temperature may affect the response of electronics in a glucometer, similar to a dose measurement system, as described above. Temperature also may affect the kinetics of chemical reaction on a test strip. Thus, a temperature sensor placed in close proximity to a glucometer and/or a test strip is important according to some embodiments.

In some embodiments, a glucometer is communicatively coupled and/or physically coupled with a dose measurement system (e.g., integrated within the housing). One or more temperature sensors may be placed on or in proximity to the glucometer in order to compensate blood glucose measurements for drift over temperature. In some embodiments, a removable and/or refillable test strip storage device is communicatively coupled and/or physically coupled with a dose measurement system (e.g., integrated within the housing) and/or a glucometer communicatively coupled and/or physically coupled with the dose measurement system. One or more temperature sensors may be placed on or in proximity to the storage device in order to identify quality issues relating to test strip temperature exposure.

In some embodiments, a communication interface on a dose measurement system or on an external device communicatively coupled with a dose measurement system is configured to communicate a status of the dose measurement system to the user, including, but not limited to, dose remaining, history of use, remaining battery life, wireless connectivity status, user reminders, and/or temperature measurements. A display, speaker, and/or vibration mechanism may be used to convey visual, audio, and/or tactile indications or alerts to a user. In some embodiments, a user input interface (e.g., a button, a switch, an alphanumeric keypad, a touch screen, a camera, and/or a microphone) allows a user to input information or instructions into a dose measurement system, including, but not limited to, initiating or ending communication between the system and a remote device, powering ON the system, powering OFF the system, resetting the system, manually inputting details of a patient behavior, and/or manually inputting details of drug delivery device usage.

FIG. 26 is a screenshot of a user interface display on a remote device (e.g., a smart phone) for initiating or ending communication between the device and one or more dose measurement systems and, once communication is initiated, for monitoring the remaining volume, battery life, and temperature of each of one or more dose measurement systems in accordance with some embodiments.

In some embodiments, when a temperature exceeds the recommended, allowed, and/or determined operating range for a drug, a user may receive a notification from the system or from an external device communicatively coupled with the system. The notification may require action by the user to be dismissed. In some embodiments, a time display tracks when a temperature event has occurred. Thus, a user may review any notifications and/or the time display to identify any temperature events in order to recalibrate the system or dispose of a drug or test strip.

CONCLUSION

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

Where methods and steps described above indicate certain events occurring in certain order, those of ordinary skill in the art having the benefit of this disclosure would recognize that the ordering of certain steps may be modified and such modification are in accordance with the variations of the invention. Additionally, certain of the steps may be performed concurrently in a parallel process when possible, as well as performed sequentially as described above. The embodiments have been particularly shown and described, but it will be understood that various changes in form and details may be made.

For example, although various embodiments have been described as having particular features and/or combination of components, other embodiments are possible having any combination or sub-combination of any features and/or components from any of the embodiments described herein. For example, although some embodiments were described as having a dose measurement system that resembled a pen cap, the dose measurement system also may be integrated with a drug delivery device. In some embodiments, vibration and/or ultrasonic waves are used to generate the signal signature instead of electromagnetic radiation. In addition, the specific configurations of the various components also may be varied. For example, the size and specific shape of the various components may be different than the embodiments shown, while still providing the functions as described herein.

The above-described embodiments can be implemented in any of numerous ways. For example, embodiments disclosed herein may be implemented using hardware, software or a combination thereof. When implemented in software, the software code can be executed on any suitable processor or collection of processors, whether provided in a single computer or distributed among multiple computers.

Further, it should be appreciated that a computer may be embodied in any of a number of forms, such as a rack-mounted computer, a desktop computer, a laptop computer, or a tablet computer. Additionally, a computer may be embedded in a device not generally regarded as a computer but with suitable processing capabilities, including a Personal Digital Assistant (PDA), a smart phone or any other suitable portable or fixed electronic device.

Also, a computer may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computer may receive input information through speech recognition or in other audible format.

Such computers may be interconnected by one or more networks in any suitable form, including a local area network or a wide area network, such as an enterprise network, and intelligent network (IN) or the Internet. Such networks may be based on any suitable technology and may operate according to any suitable protocol and may include wireless networks, wired networks or fiber optic networks.

The various methods or processes outlined herein may be coded as software that is executable on one or more processors that employ any one of a variety of operating systems or platforms. Additionally, such software may be written using any of a number of suitable programming languages and/or programming or scripting tools, and also may be compiled as executable machine language code or intermediate code that is executed on a framework or virtual machine.

Also, various inventive concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All publications, patent applications, patents, and other references mentioned herein are incorporated by reference in their entirety.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The invention claimed is:

1. An apparatus, comprising:
   a light source disposed and configured to emit electromagnetic radiation toward a container containing a volume of a drug;
   a plurality of sensors optically coupleable to the light source, each sensor of the plurality of sensors disposed and configured to detect a portion of the electromagnetic radiation emitted by the light source;
   a temperature sensor disposed and configured to measure at least one temperature associated with the drug in the container; and
   a processor configured to:
      receive, from each sensor from the plurality of sensors, data representative of electromagnetic radiation detected by that sensor;
      receive, from the temperature sensor, data representative of the at least one measured temperature;
      adjust the data received from each sensor from the plurality of sensors based on the at least one measured temperature to produce compensated data; and
      convert the compensated data into a signature including a plurality of values representative of the electromagnetic radiation detected by each sensor from the plurality of sensors.

2. The apparatus of claim 1, wherein the processor is further configured to:
   compare the at least one measured temperature to a temperature guideline to determine whether a temperature event has occurred; and
   send, via a communication interface operatively coupled to the processor, a notification based on the temperature event to a computer device remote from the processor.

3. The apparatus of claim 2, wherein the temperature guideline includes at least one of: a baseline temperature, a maximum temperature, and a minimum temperature.

4. The apparatus of claim 3, wherein the temperature guideline further includes at least one of: an amount of one-time exposure above the maximum temperature, an amount of one-time exposure below the minimum temperature, an amount of cumulative exposure above the maximum temperature, an amount of cumulative exposure below the minimum temperature, a maximum rate of temperature change, and a maximum frequency of temperature fluctuations.

5. The apparatus of claim 2, wherein the temperature guideline is specific to at least one of the container and the drug.

6. The apparatus of claim 2, wherein the temperature event is at least one of a relationship and a difference between the at least one measured temperature and the temperature guideline.

7. The apparatus of claim 2, wherein the processor is further configured to determine, based on the temperature event, at least one of: a level of efficacy of the drug, a level of safety of the drug, a level of comfort of a user of the drug, and an expiration status associated with the drug.

8. The apparatus of claim 1, wherein the processor is further configured to:
   determine dose information associated with the drug based at least on the signature; and
   send, via a communication interface operatively coupled to the processor, the dose information to a computer device remote from the processor.

9. The apparatus of claim 8, wherein the dose information associated with the drug includes at least one of: a volume of the drug in the container, a volume of a dose of the drug dispensed from the container, a number of doses of the drug in the container, a number of doses of the drug dispensed from the container, a time of last dose, and a scheduled time for a dose.

10. A method, comprising:
    causing at least one light source to emit electromagnetic radiation toward a container containing a volume of a drug;
    detecting, with each sensor from a plurality of sensors, a portion of the electromagnetic radiation emitted by the at least one light source through the drug container;
    measuring at least one temperature associated with the drug with a temperature sensor;
    adjusting data representative of the portion of the electromagnetic radiation detected by each sensor from the plurality of sensors based on the at least one measured temperature to produce compensated data;
    converting the compensated data into a signature including a plurality of values representative of the electromagnetic radiation detected by the plurality of sensors; and
    determine dose information associated with the drug based at least on the signature.

11. The method of claim 10, wherein the dose information is determined based on the signature and information derived from electromagnetic energy signatures previously recorded for a range of volumes of the drug in the container.

12. The method of claim 10, wherein the dose information includes at least one of: a volume of the drug in the container, a volume of a dose of the drug dispensed from the container, a number of doses of the drug in the container, a number of doses of the drug dispensed from the container, a time of last dose, or a scheduled time for a dose.

13. The method of claim 10, further comprising comparing the at least one measured temperature to a temperature guideline to determine whether a temperature event has occurred.

14. The method of claim 13, wherein the temperature guideline includes at least one of: a baseline temperature, a maximum temperature, and a minimum temperature.

15. The method of claim 13, wherein the temperature guideline is specific to at least one of the container or the drug.

16. The method of claim 13, wherein the temperature event is at least one of a relationship and a difference between the at least one measured temperature and the temperature guideline.

17. The method of claim 13, further comprising determining, based on the temperature event, at least one of: a level of efficacy of the drug, a level of safety of the drug, a level of comfort of a user of the drug, and an expiration status associated with the drug.

18. A system, comprising:
- a container containing a volume of a drug; and
- a measurement device configured to be removably coupleable to the container, the measurement system including:
  - a light source disposed and configured to emit electromagnetic radiation toward the container;
  - a plurality of sensors optically coupleable to the light source, each sensor of the plurality of sensors disposed and configured to detect a portion of the electromagnetic radiation emitted by the light source;
  - a temperature sensor disposed and configured to measure at least one temperature associated with the drug in the container; and
  - a processor configured to:
    - receive, from each sensor of the plurality of sensors, data representative of electromagnetic radiation detected by that sensor;
    - receive, from the temperature sensor, data representative of the at least one measured temperature;
    - adjust the data received from each sensor of the plurality of sensors based on the at least one measured temperature to produce compensated data; and
    - convert the compensated data into a signature including a plurality of values representative of the electromagnetic radiation detected by each sensor from the plurality of sensors.

* * * * *